US006191862B1

(12) United States Patent
Swanson et al.

(10) Patent No.: US 6,191,862 B1
(45) Date of Patent: Feb. 20, 2001

(54) METHODS AND APPARATUS FOR HIGH SPEED LONGITUDINAL SCANNING IN IMAGING SYSTEMS

(75) Inventors: Eric A. Swanson, Acton; Christopher L. Petersen, Carlisle, both of MA (US)

(73) Assignee: Lightlab Imaging, LLC, Westford, MA (US)

(*) Notice: Under 35 U.S.C. 154(b), the term of this patent shall be extended for 0 days.

(21) Appl. No.: 09/233,421

(22) Filed: Jan. 20, 1999

(51) Int. Cl.[7] .................................................. G01B 9/02
(52) U.S. Cl. .............................. 356/450; 356/511
(58) Field of Search ..................... 356/345, 347

(56) References Cited

U.S. PATENT DOCUMENTS

| | | | |
|---|---|---|---|
| 3,776,637 | 12/1973 | Hecht | 356/106 |
| 4,179,219 | * 12/1979 | Smith | 356/346 |
| 5,007,721 | 4/1991 | Morris et al. | 350/486 |
| 5,033,853 | 7/1991 | Frangineas, Jr. | 356/345 |
| 5,062,150 | 10/1991 | Swanson et al. | 359/152 |
| 5,321,501 | 6/1994 | Swanson et al. | 356/345 |
| 5,387,969 | 2/1995 | Marantette | 356/4.5 |
| 5,459,570 | 10/1995 | Swanson et al. | 356/345 |
| 5,465,147 | 11/1995 | Swanson | 356/345 |
| 5,491,524 | 2/1996 | Hellmuth et al. | 351/212 |
| 5,619,368 | 4/1997 | Swanson | 359/326 |
| 5,748,598 | 5/1998 | Swanson et al. | 369/94 |
| 5,751,419 | * 5/1998 | Takahashi et al. | 356/321 |
| 5,784,352 | 7/1998 | Swanson et al. | 369/94 |
| 5,892,583 | * 4/1999 | Li | 356/345 |
| 5,994,690 | * 11/1999 | Kulkarni et al. | 250/216 |

FOREIGN PATENT DOCUMENTS

| | | |
|---|---|---|
| 60-129614 | 7/1985 | (JP). |
| 697809 | 11/1979 | (RU). |
| WO 95/33970 | 12/1995 | (WO). |
| WO 97/32182 | 9/1997 | (WO). |
| WO 98/35203 | 8/1998 | (WO). |
| WO 98/38907 | 9/1998 | (WO). |

OTHER PUBLICATIONS

E. A. Swanson, "Optical Coherence Tomography: Principles, Instrumentation, and Biological Applications", Biomedical Optical Instrumentation and Laser–Assisted Biotechnology, Nov. 10–22, Erice, Italy (1995).

D. Huang et al. "Optical Coherence Tomography", Science, 254, 1178–1181 (1991).

K. Takada et al. "New Measurement System for fault Location in Optical Waveguide Devices Based on and Intererometric Technique", Applied Optics, 26, 1603–1606, May, 1, 1987.

J. Szydlo et al. "Air–Turbine Driven Optical Low–Coherence Reflectometry at 28.6kHz Scan Repetition Rate", Optics Communications, (Aug. 15, 1998), pp. 1–4.

J. Ballif et al. "Rapid and Scalable Scans at 21 m/s in Optical Low–Coherence Reflectometry", Optics Letters, vol. 22, No. 11, Jun. 1, 1997, pp. 757–759.

* cited by examiner

Primary Examiner—Frank G. Font
Assistant Examiner—Phil Natividad
(74) Attorney, Agent, or Firm—Fleshner & Kim, LLP

(57) ABSTRACT

An imaging system wherein an optical signal is transmitted to both a sample to be measured and a rotating element which is calibrated to the system. A return signal is detected by the system, and a scan analyzer and correction unit uses the system calibration information along with synchronization information to correct for return signal degradation or errors due to imperfections in the rotating element in real time. This allows for an accurate measurement of the sample. The system can also include a coarse path-length adjustment unit to allow the system to track a region of interest within a sample to further allow for accurate sample measurement.

23 Claims, 26 Drawing Sheets

Without region-of-interest tracking

With region-of-interest tracking

Use of Rotating Element in Double-Pass Geometry

Rotating Helical Mirror

1

METHODS AND APPARATUS FOR HIGH SPEED LONGITUDINAL SCANNING IN IMAGING SYSTEMS

BACKGROUND OF THE INVENTION

1. Field of the Invention

The field of invention relates to high speed scanning of an optical delay and more specifically to a method and apparatus for performing high-speed scanning of an optical delay for an Optical Coherence Tomography (OCT) imaging system.

2. Background of the Related Art

Optical coherence tomography (OCT) is a new imaging modality. OCT has the ability to perform high resolution, high-sensitivity, cross sectional imaging of microstructures. The use of OCT has several significant advantages over standard optical imaging techniques and ultrasound. First, OCT can directly measure cross-sectional microstructure on a micron scale. Second, OCT can perform imaging of structures in situ and without contact. Third, imaging can be performed in real time, and fourth, OCT technology is fiber optically based and can be interfaced with a wide range of medical, microscopic, or industrial applications.

OCT is analogous to ultrasound B mode imaging, except that it uses light rather than sound and performs imaging by measuring the backscattered intensity of light from a microstructure. OCT produces one, two, or three dimensional images by directing an optical beam at an object to be imaged, and measuring backscattered light as the beam is scanned across the object. The OCT image is a gray scale or false color two dimensional representation of backscattered light intensity in a cross sectional plane. In medical imaging, the OCT image represents the differential backscattering contrast between different tissue types on a micron scale.

There are a variety of interferometric embodiments for OCT systems. One typical implementation uses a fiber optic coupler for the Michelson interferometer. One of the arms of the interferometer is used to deliver and scan the optical beam on a sample, while the other arm functions as a reference arm and has a high speed longitudinal scanning mechanism. When the path-length to a reflection site within the sample is matched to the reference arm path-length, optical interference occurs at the photodetector. The interference signal is detected, demodulated, processed, and stored and/or displayed to yield the backscattered light intensity versus depth for a given transverse position of the incident beam.

The longitudinal scanning mechanism is a key technology for OCT systems. A requirement of many OCT systems is to achieve a near uniform-velocity longitudinal scanner, with high-speed, and high duty cycle. Presently, most commercial OCT systems use either a small moving retro-reflector mounted onto a galvanometric beam steerer or a fiber stretcher using PZT actuators. Techniques demonstrated to date do not meet system needs for certain applications that require high-speed scanning, such as real-time medical endoscopic procedures.

Previous work has identified the concept of a rotating CAM to perform longitudinal scanning. Hecht (U.S. Pat. No. 3,776,637) has described the use of a circular involute reflector for providing a variable path-length reference arm, and its use in an interferometer for a Fourier spectrometer. Hecht, however, fails to describe the use of this concept in an OCT system and the unique features associated with this use, nor does Hecht disclose any other rotating mechanisms for delay line scanning. Tasaka (Japanese Patent Application No. 58-24005) discloses a CAM for use as a potentiometer and its use with a measuring interferometer. Tasaka, however, describes a radius that varies in proportion to the angle of rotation. Such a device will not ensure a retro-reflected beam, which is a condition necessary for OCT. Marantette (U.S. Pat. No. 5,387,969) relates to using a rotating CAM for blocking light incident on a photo-detector and other applications. Morris et al. (U.S. Pat. No. 5,007, 721) is directed to a mechanically rotated Doppler frequency shifter that uses a spiral embodiment for path-length adjustment. The embodiment described therein is very difficult to fabricate. Frangineas (U.S. Pat. No. 5,033,853) discloses an apparatus for autocorrelating optical radiation signals which is used in an optical correlator. The basic embodiment of this device, however, cannot be driven to high speeds because of the required linkage to a moving corner cube.

Presently, there are no commercially available high-speed longitudinal (path-length) scanning devices for use in OCT systems, despite the intense need for such devices to address important medical markets. None of the related art addresses details on the use of a rotating element, such as a CAM (or other devices described in this disclosure), in an OCT system, nor do they address the unique optical alignment issues, manufacturing issues, and timing, calibration, and correction techniques required for use in OCT systems. Further, the related art fails to address critical design issues such as the need for techniques to fabricate, calibrate, and overcome operational imperfections in real-time to achieve high resolution OCT imaging capability, or other aspects unique to OCT systems.

As described above, the related art has various disadvantages. First, the disclosed systems are not scalable to the faster image rates required for medical and other "high-end" markets where motion induced artifacts from a slow imaging rate can destroy resolution or throughput speeds in on-line nondestructive evaluation (NDE) applications. Also, an inherent difficulty in most of the related art is the repetitive starting and stopping a mass at high speed. This can cause non-uniform scanning velocity which requires non-uniform Doppler signal processing requirements, forcing complex receiver circuitry and, more importantly, significant inefficiencies in signal-to-noise ratio and image acquisition rate. Degradations can exceed 10 dB from ideal. Also, retro-reflectors can be massive and therefore high speed cannot be achieved. Additionally, the translation from the angular motion of a Galvanometer shaft to displacement of the retro-reflector is not linear.

The above references are incorporated by reference herein where appropriate for appropriate teachings of additional or alternative details, features and/or technical background.

SUMMARY OF THE INVENTION

Accordingly, it is an object of this invention to provide an imaging system that substantially overcomes at least one of the aforementioned problems caused by disadvantages in the prior art. It is another object of the invention to provide a longitudinal scanner using rotating elements, which has the features of high speed, ability to program a variety of speeds, linearity, and repeatability. The scanner can have a scan range of greater than 3 mm, and an image acquisition rate of between 1 and 30 frames, or more, per second, which is required by many OCT markets.

It is another object of the invention to provide an imaging system that is scalable, efficient in terms of signal-to-noise ratio and image acquisition rate, minimizes receiver complexity, and can benefit from the large rotational motor technology base.

It is another object of this invention to provide a high-speed rotational motion apparatus with a surface that alters an incident optical beam so as to produce a near linearly changing optical path-length and a nearly constant intensity as a function of rotation angle.

It is another object of this invention to provide a rapidly varying optical path-length in an OCT imaging system to produce high-speed nearly-uniform longitudinal scanning and associated optical images of a sample optical properties.

It is another object of this invention to provide methods of calibrating, triggering, and synchronizing to allow motor control and/or the synchronous acquisition of the OCT image.

It is another object of this invention to provide a scan correcting processor to correct for imperfections in the manufacturing of the optical surface or other parts of the longitudinal scanner by applying predetermined (and fixed) path-length corrections, in real-time, as the device is driven.

It is another object of this invention to provide techniques to fabricate, calibrate, and overcome operational imperfections in real-time so as to achieve high resolution OCT imaging capability.

It is another object of this invention to provide a longitudinal path-length correction mechanism to allow for adjusting the sample arm distance beyond the stroke of the high-speed scanner at rates including the horizontal frame rate of the OCT imaging systems.

In order to achieve at least some of the above objects in whole or in part, there is provided an imaging system which uses a path-length delay mechanism to produce images. The delay mechanism translates rotational motion to generate optical delay, and calibrates imperfections in the optical delay mechanism in real-time using calibration techniques.

More specifically, there is provided an apparatus for performing scanning of an optical delay in an OCT or other interferometric imaging or ranging system, where the apparatus can be adapted to first receive an optical signal from the imaging system and rapidly and repetitively adjust the optical delay of the optical signal prior to returning the optical signal to the imaging system. In one embodiment, the apparatus can include a motor capable of rotational motion, which is in mechanical communication with at least one optical element in optical communication with the optical signal. In another embodiment, the mechanical communication translates the rotational motion of the motor into a nearly linear delay of the optical signal via movement of the optical element(s). In one embodiment of the invention, the apparatus further includes a synchronization system in electrical communication with the imaging system, and the apparatus can be calibrated to account for imperfections in the path length scanning. The synchronization system and calibration information can be used by the imaging system to compensate for the imperfections in the path length scanning in real-time.

In one variation of this embodiment, the optical element(s) could be a multi-segment CAM configured in either single-pass or double pass-geometry. Using the CAM embodiment, the imaging system includes a broadband optical source in optical communication with an interferometer. The interferometer couples light from the source to a sample probe module, and the sample probe module couples the light onto a sample and collects light altered by the sample. The interferometer also couples light to a reference-arm module, and the reference-arm module couples light onto a multi-segment rotating CAM with a mirrored surface. It then collects light altered in a predetermined fashion by the rotating CAM. The CAM surface is designed to produce a nearly linear time-varying repetitive scanning of the optical delay from the reference-arm module to the surface of the CAM. The interferometer is also in optical communication with a detector, which detects optical interference between light altered by the sample and light altered by the rotating CAM. Further, the detector is in electrical communication with a processor, which includes a synchronization system that monitors the specific segment of the CAM is undergoing illumination, and uses information stored in a calibration table to correct for imperfections on the CAM surface in real-time. The result is a high-resolution image of the sample's optical properties.

Alternatively, the optical element(s) could be a rotating helical mirror. In yet another variation, the optical element(s) could be a transmissive rotating disc. This disc could also have an index-of-refraction that varies in angle, and could alternatively be reflective instead of transmissive.

Another alternative is for the optical element(s) to be a reflective surface that is attached to a rotating belt. Also, in another variation, the optical element(s) could be a mirrored surface used in conjunction with a galvanometric motor. In this variation, the mirrored surface is designed to retro-reflect the central ray of said optical signal. It is also possible to cause the galvanometric motor to be driven at mechanical resonance.

These above mentioned embodiments can also include a path-length correction mechanism that allows for coarse adjustment of the optical delay in addition to the rapid adjustment, wherein the coarse adjustment is used to track the region-of-interest within a sample.

Additionally, in order to achieve at least some of the above objects in whole or in part, there is provided an apparatus for altering the optical delay of a light beam that translates rotational motion into optical delay, calibrates imperfections in the optical delay mechanism, and corrects imperfections in real-time using a calibration technique and algorithm.

In one embodiment, the apparatus for performing scanning of an optical delay of an optical signal can include an input port to receive the optical signal and an output upon which to return the delayed optical signal. The apparatus can also contain at least one optical element in optical communication with the optical signal and in mechanical communication with a motor capable of rotational motion. The mechanical communication transforms the rotational motion into a nearly linear delay of the optical signal. Also, because the optical delay may have imperfections due to machining tolerances or other effects, the apparatus includes a synchronization system which tracks the motion of the optical element(s), and calibrates the delay imperfections to the synchronization system. The synchronization system and calibration information are then used to compensate for the imperfections in the path length scanning in real-time.

The optical element(s) in the above embodiment could be a multi-segment CAM, which can be used in either a single pass or a double-pass configuration. Alternatively, the optical element could be a rotating helical mirror. In yet another variation, the optical element could be a transmissive rotating disc. This disc could also have an index-of-refraction that varies in angle, and could alternatively be reflective instead of transmissive.

Another alternative to this embodiment is for the optical element(s) to be a reflective surface attached to a rotating belt. Also, in another variation, the at least one optical element could be a mirrored surface used in conjunction with a galvanometric motor. In this scenario, the mirrored surface is designed to retro-reflect the central ray of said optical signal.

Further, in order to achieve at least some of the above objects in whole or in part, there is provided an OCT imaging system including an optical radiation source in communication with an interferometer, where the interferometer couples light onto a sample and collects light altered by the sample. The interferometer also couples light to a scanning optical delay mechanism, where the scanning optical delay has a scan-range and a center-of-scan. The system also includes a beam combining mechanism for combining the light altered by the sample and light altered by the scanning optical delay mechanism. Additionally, the system contains a detector for detecting the combined light, where the detector is in communication with a signal processor, and the signal processor produces images of the samples' optical properties. The processor also detects features in the samples and adjusts the center-of-scan so that the scan range covers the scan region-of-interest.

Additionally, in order to achieve at least some of the above objects in whole or in part, there is provided an apparatus for performing scanning of an optical delay in an OCT or other interferometric imaging or ranging system, where the apparatus receives an optical signal from the imaging system and rapidly and repetitively adjusts the optical delay of the optical signal prior to returning the optical signal to the imaging system. The apparatus contains a motor capable of rotational motion, and the motor is in mechanical communication with at least one optical element in optical communication with the optical signal. The mechanical communication translates the rotational motion of the motor into nearly linear delay of the optical signal via movement of the at least one optical element. The apparatus further includes a synchronization system in electrical communication with the imaging system, and the apparatus is calibrated to account for imperfections in the path length scanning. The synchronization system and calibration information are used by the imaging system to compensate the imperfections in the path length scanning in real-time.

Moreover, to achieve at least the above in whole or in parts there is provided an apparatus, comprising an interferometer which receives broadband light and outputs a reference output signal and a probe signal directed to a sample which produces a sample return signal, an optical path-length scanning unit which receives the reference output signal and outputs a reference return signal to the interferometer, the interferometer combining the reference return signal and the sample return signal and outputting an interferometer output signal, a detector unit for receiving the interferometer output signal and outputting a detector output signal, a scan analyzer and correction unit coupled to the detector unit including an optical path-length position unit for receiving the detector output signal, and a scanning unit controller coupled to the optical path-length scanning unit, for controlling the optical path-length scanning unit and for outputting a controller signal to the scan analyzer and correction unit, wherein the scan analyzer and correction analyzes the controller signal and the detector output signal and determines scan correction information.

To achieve at least the above in whole or in parts, there is also provided an apparatus, comprising an interferometer which receives broadband light and outputs a reference output signal and a probe signal directed to a sample which produces a sample return signal, a rotating optical path-length scanning unit which receives the reference output signal and outputs a reference return signal to the interferometer, the interferometer combining the reference return signal and the sample return signal and outputting an interferometer output signal, a detector unit for receiving the interferometer output signal and outputting a detector output signal, a scan analyzer and correction unit coupled to the detector unit including an optical path-length position unit for receiving the detector output signal, and a scanning unit controller coupled to the rotating optical path-length scanning unit, for controlling the rotating optical path-length scanning unit and for outputting a controller signal to the scan analyzer and correction unit, wherein the scan analyzer and correction analyzes the controller signal and the detector output signal and determines scan correction information.

To achieve at least the above in whole or in parts, there is also provided an optical path-length varying device, comprising at least one reflector for receiving light and reflecting the light as return light, a belt coupled to the at least one reflector capable of translating the at least one reflector, and a unit for moving the belt to induce translation of the at least one reflector, wherein the path-length traveled by the return light varies as a function of the translation of the at least one reflector.

To achieve at least the above in whole or in parts, there is also provided an optical path-length varying device, comprising a disc capable of spinning about an axis and having a face for receiving light and reflecting the light as return light, and a unit for rotating the disc about the axis, wherein the face of the disc is shaped so that as the disc rotates about the axis, the path-length traveled by the return light varies.

To achieve at least the above in whole or in parts, there is also provided an optical path-length varying device, comprising a disc capable of spinning about an axis and having a first face and a second face, wherein light is received at the first face and transmitted through the disc to the second face, a reflector for reflecting the light as return light, and a unit for rotating the disc about the axis, wherein the path-length traveled by the return light varies as the disc rotates about the axis, thereby producing a varying path-length.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements.

DETAILED DESCRIPTION OF PREFERRED EMBODIMENTS

Figure 1A:
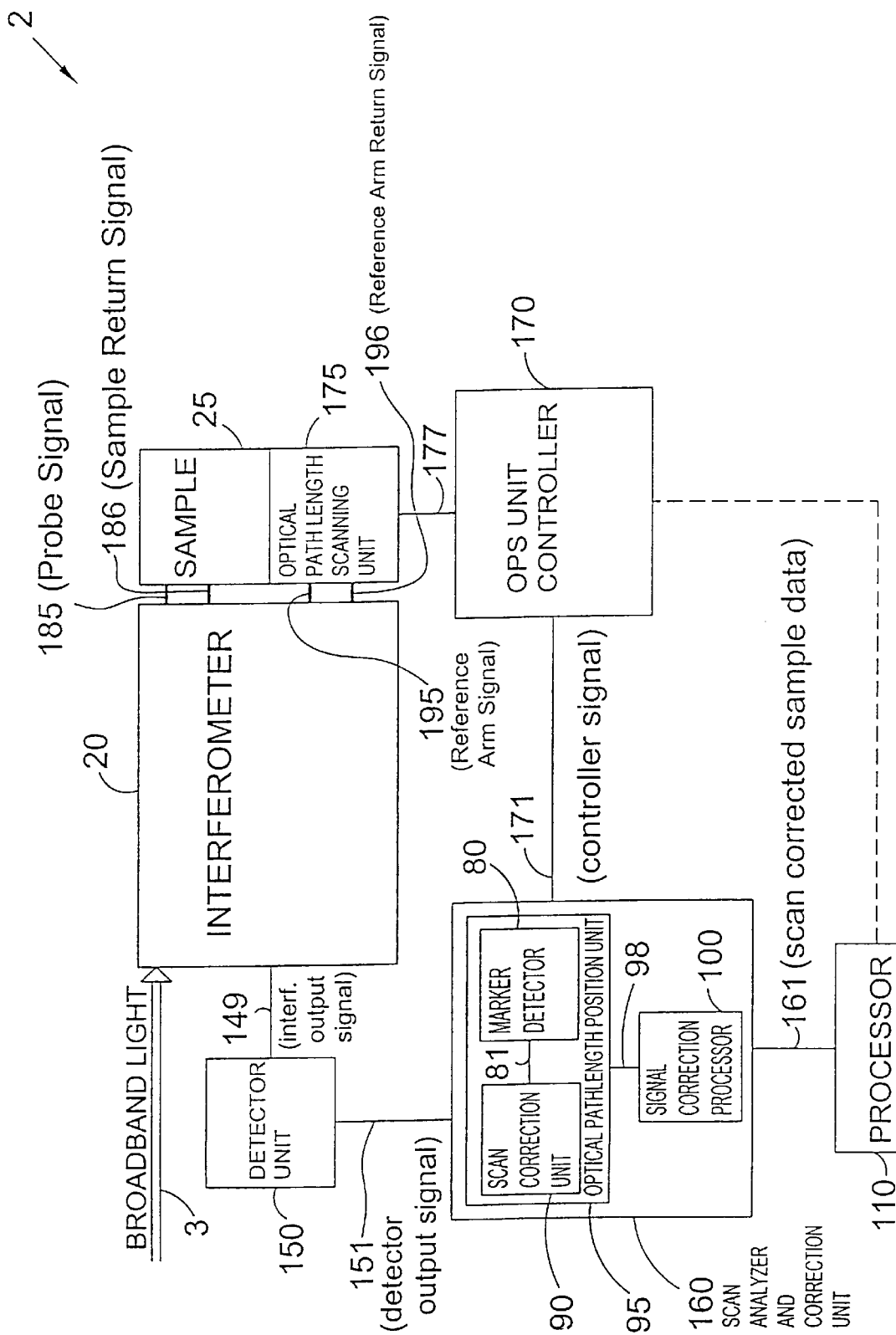
FIG. 1A is a drawing showing an embodiment of an imaging system.

FIG. 1A shows one embodiment of an imaging system 2 according to this invention. Interferometer 20 receives broadband light 3 and outputs a probe signal 185 which is received by sample 25. Sample 25 thereafter returns a sample return signal 186 to the interferometer 20. Interferometer 20 also outputs a reference output signal 195, which is received by Optical Path-length Scanning (OPS) unit 175. OPS unit 175 thereafter produces reference return signal 196 which is received by interferometer 20. Although FIG. 1A shows a space between the interferometer 20 and the OPS unit and sample, the interferometer of this embodiment can extend to the sample and the OPS unit. Although shown as separate signals, probe signal 185 and reference output signal 195 may comprise one signal 185' (not shown) which serves as both probe signal 185 and reference output signal 195. An example of such an embodiment includes signal 185', which first hits a partially transmissive OPS unit 175, and continues on to the sample 25. For simplicity, a system using a separate probe signal 185 and reference output signal 195 will be discussed.

The interferometer 20 combines signals 186 and 196, and outputs an interferometer output signal via line 149 to detector unit 150. Detector unit 150 then produces detector output signal on line 151, which is received by scan analyzer and correction unit 160 and further received by optical path-length position unit 95. It should be understood that although the term "line" is used to describe the connection between elements, any suitable connection may be used, such as fiber optics, coaxial cable, and radio frequency transmission, among others.

The scan analyzer and correction unit 160 also receives information from an OPS unit controller 170 on line 171 and inputs that information to optical path-length position unit 95. The OPS unit controller 170 is coupled to OPS unit 175 via coupling 177. Using the information in the controller signal and the detector output signal on line 151, the optical path-length position unit 95 generates scan correcting data. It should be noted that although this embodiment and others are described and depicted as having several functional elements to perform processing, analysis, and control, these sub-systems could be combined into a single sub-system or circuit, or could be split into any number of sub-systems or circuits.

According to one embodiment of the invention, the optical path-length position unit 95 includes a scan correction unit 90 and a marker detector 80. The marker detector 80 receives and analyzes the controller signal from the OPS unit controller 170 and outputs marker information via coupling 81 to the scan correction unit 90. Scan correction unit 90 also receives the detector output signal from the detector unit 150. Scan correction unit 90 uses these two signals to determine the necessary scan correction, and generates scan correcting data. The scan analyzer and correction unit 160 also includes a signal correction processor 100 which receives the scan correcting data via coupling 98 and modifies the detector output signal using the scan correcting data, outputting scan corrected sample data on line 161. The scan corrected sample data can be received by a processor 110, where it can be further analyzed or displayed on a screen.

Figure 1B:
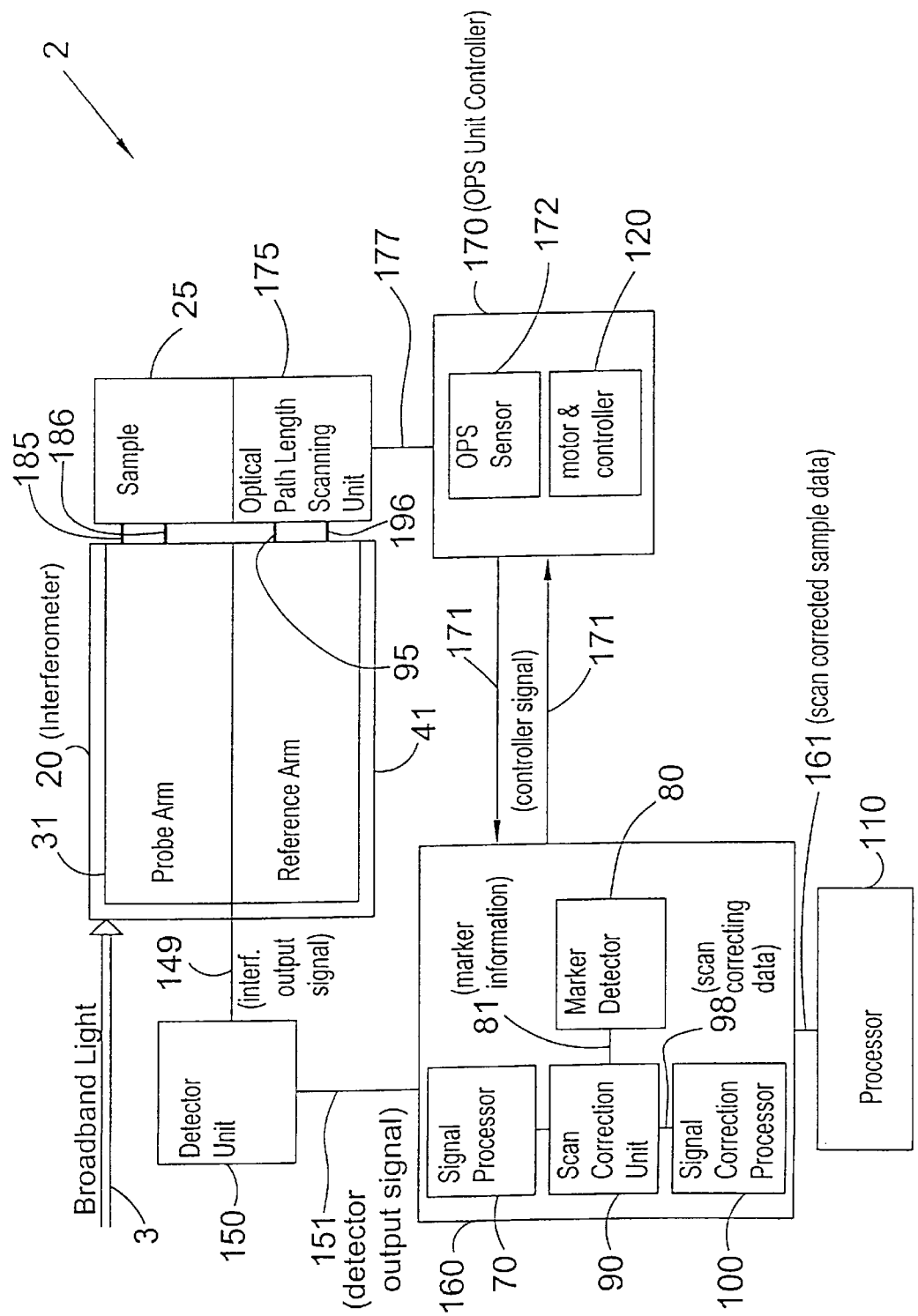
FIG. 1B is a drawing showing another embodiment of an imaging system.

FIG. 1B shows additional detail of the OCT system 2 according to one embodiment of the invention. The OPS unit controller 170 includes OPS unit position sensor 172 and motor and controller unit 120. OPS unit position sensor 172 receives information from OPS unit 175 regarding which part of the OPS unit is receiving a signal 195. OPS unit controller 170 then passes the information regarding the positioning of OPS unit 175 to scan analyzer and correction unit 160. Additionally, OPS unit controller 170 may receive feedback from scan analyzer and correction unit 160. The motor and controller unit 120 regulates the speed of the OPS unit 175.

Scan analyzer and correction unit 160 includes a first signal processor 70, scan correction unit 90, signal correction processor 100, and marker detector 80. Signal processor 70 acts to filter, detect, and digitize the detector output signal from the detector unit 150. Signal correction processor 100 analyzes data from scan correction unit 90 and compensates for imperfections in OPS unit 175, resulting in corrected sample data.

Interferometer 20 can include a probe arm 31 and a reference arm 41. The probe arm 31 couples a probe signal 185 onto a sample 25, while the reference arm 41 couples a reference arm signal 195 onto the OPS unit 175. Alternatively, interferometer 20 can include only one arm which scans both the sample 25 and the OPS unit 175. For simplicity, the descriptions in that follow describe an interferometer with distinct arms, although any interferometer could be substituted.

Figure 1C:
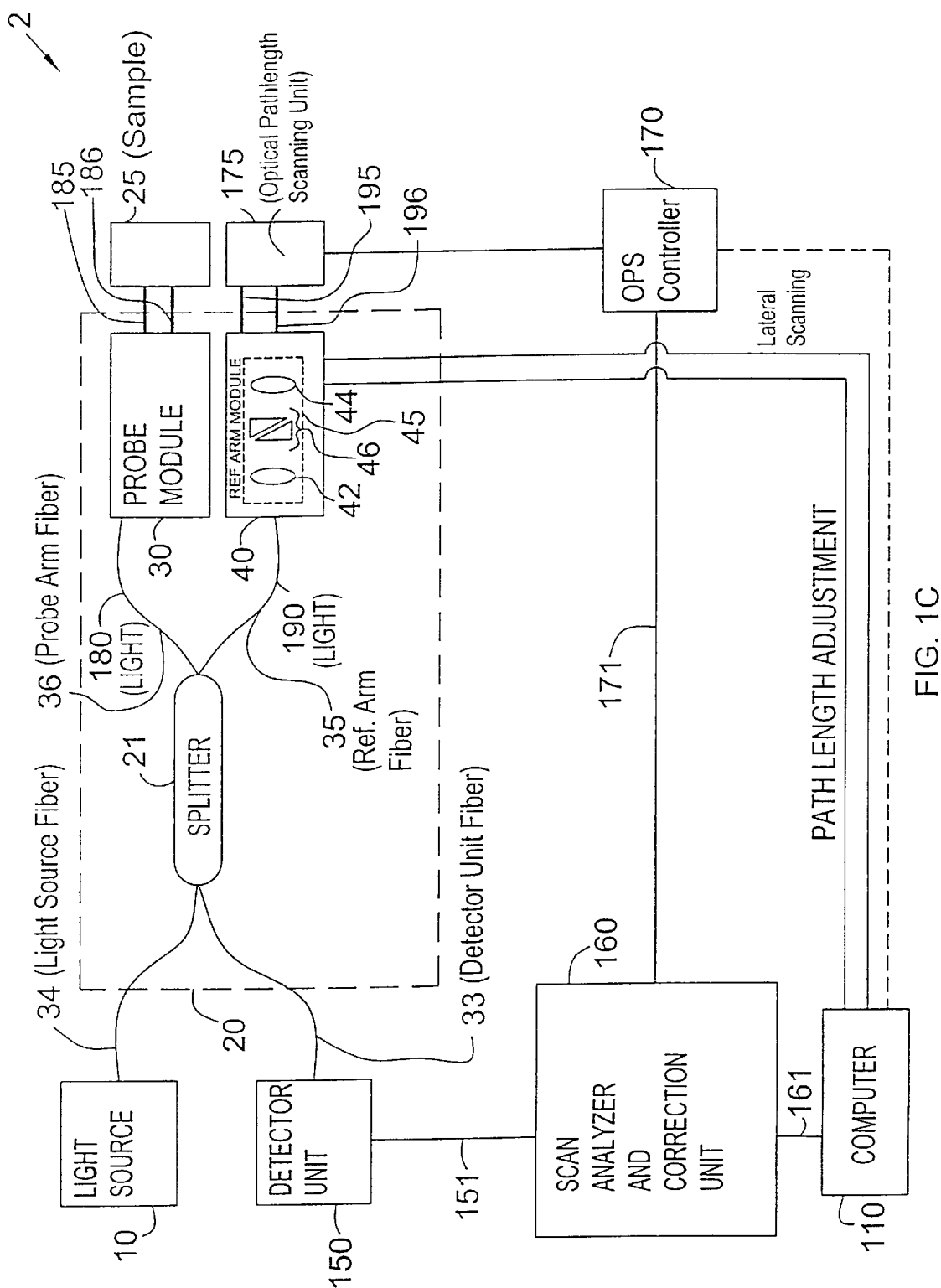
FIG. 1C is a drawing showing another embodiment of an imaging system.

FIG. 1C shows other features of the imaging system 2 according to one embodiment of the invention. A light source 10 provides broadband light through light source fiber 34. Broadband light is defined as light which has a bandwidth which yields the desired resolution in the Z direction for the system 2. The smaller the coherence length of the broadband light, the higher the resolution measurement of the system.

Light source 10 delivers broadband light to splitter 21 via light source fiber 34. Splitter 21 splits the broadband light into a first portion of split input light 180 and a second portion of split input light 190. The first portion 180 is provided to the probe module 30 by way of probe arm fiber 36. The second portion 190 is provided to reference arm module 40 by way of reference arm fiber 35. Reference arm module 40 includes a coarse path-length adjustment mechanism 45, shown generally as a dashed box, which is controlled by a computer 110. The coarse path-length adjustment mechanism 45, a particular embodiment of which is region-of-interest-tracking, allows for altering the measurement position within the sample, or for accommodating different types of probe modules that may have differing optical delays. There are a variety of methods to change the focal point, some of which will be discussed later. The coarse path-length adjustment need not be fast with respect to the OPS unit 175. Methods for coarse path-length adjustment include, for example, changing the path-length by moving lens 44 or lens 42 right or left as shown in FIG. 1C. Generally, it is useful to fix the distance from fiber 35 to lens 42 and move them together as a unit left or right, thereby changing the distance between lens 42 and 46. In this example, the first lens 42 collimates the reference light 190 and the second lens 44 focuses light onto the surface of the OPS unit 175. Since the light is collimated between the two lenses, there is minimal loss in power if the distance between the lenses is adjusted. Alternatively, the properties of the fibers 35, 36 can be altered in ways known in the art, such as by slightly altering one or both of their indices of refraction, or stretching a spool of fiber, etc., so as to change the resulting optical path-length. Also, the prism pair 46 of the reference arm module 40 can be used to vary the optical path-length. There are other methods of changing the coarse optical path-length known in the art, any of which can be used to achieve this result. Also, the coarse path-length adjustment feature allows for the ability to perform region-of-interest tracking, as will be described in a later section.

Interferometer 20 receives signals 186 and 196 from the sample 25 and the OPS unit 175 respectively, and combines them to produce the interferometer output signal. The interferometer output signal is delivered to detector unit 150 by way of detector unit fiber 33.

More specifically, in this embodiment, the interferometer 20 has two arms, namely a sample arm (also known as a probe arm) 31 and a reference arm 41 (FIG. 1B). It should be noted that the interferometer shown is by way of example, and any interferometer could be substituted.

The sample arm 31 couples the first portion of split input light 180 light into a probe module 30. The probe module 30 has optics to couple light 185 onto the sample 25 and couple light altered by the sample back into the sample arm 31 (FIG. 1B). The probe module 30 also has a one-dimensional or two-dimensional transverse scanning mechanism to scan the light 185 laterally along the sample 25 to produce two-dimensional or three-dimensional images. Alternatively, the sample can be scanned such as in the manufacturing of polymer films in a web inspection application. In that case, the probe is fixed and the sample 25 moves so as to be scanned. Examples of probe modules can include microscopes, catheters, endoscopes, laparoscopes, hand-held probes, probes for injection molding machines, and web inspection machines, among others.

The reference arm fiber 35 couples the second portion of split input light 190 to a reference arm module 40. This module contains optics to couple light from the reference arm fiber to OPS unit 175. Note that the OPS unit can have a multitude of different surface types, as will be described in a subsequent section. Additionally, the motion of the OPS unit can be rotational, translational, or a combination of both. The reference arm module 40 also has the ability to adjust the coarse path-length, as described previously, by adjusting the optical path-length between two lenses 42, 44.

It is important that dispersion be balanced between the sample arm 31 and reference arm 41. The reference arm module 40 in the reference arm (or the probe module 30 in the sample arm 31) can contain a prism pair 46 or other suitable devices to match dispersion. Alternatively, with phase sensitive synchronous detection at the receiver, dispersion can be compensated for electronically as is known in the art.

The reflected light 186 and 196 is combined and passes out of the interferometer 20 and through detector unit 150. The detector unit 150 detects and amplifies the signals from the interferometer 20, and passes the signal to a scan analyzer and correction unit 160, which controls the synchronization of the lateral scanning in the probe module 30 with the longitudinal scanning of the reference module in conjunction with OPS controller 170 and computer 110. Synchronization is necessary to perform accurate measurements of the sample 25. The synchronization is dependent on proper calibration of the OPS unit 175, and although calibration need not necessarily be performed in real time, correction is preferably performed in real time, as described below.

The nominal motor speed can be generated from an on-board clock or can be commanded from the computer 110. The OPS unit controller 170 has a once-per-revolution (1/Rev) sensor and an optional multiple-pulse-per-revolution (M/Rev) sensor or other suitable means for determining a fixed point(s) on the OPS unit 175. These sensors can be any type of sensor, including optical, electromagnetic, magnetic, electronic, capacitive, mechanical, or any other type known in the art. The OPS sensor 172 (FIG. 1B) of the OPS controller 170, in combination with the scan analyzer and correction unit 160, keeps track of the position of the OPS unit 175. Using the scan analyzer and correction unit 160, imperfections in the OPS unit can be corrected in real-time. This can be done using an optical encoder or several other methods including pattern recognition algorithms. Methods of calibration will be discussed in a subsequent section.

The basic concept of the system is that light is focused onto the OPS unit 175, which rotates, translates, or otherwise moves, at a speed regulated by the OPS unit controller 170 in conjunction with the scan analyzer and correction unit 160. Light is subsequently delivered back into the reference arm fiber 35. As the OPS unit 175 moves at a uniform, but selectable speed, the optical path-length is scanned in a uniform manner, thus achieving an approximately constant Doppler shift. This Doppler shift is demodulated by the detector unit 150, and used to determine measurement of the sample 25. Non-constant Doppler frequency shifts are also possible and can be demodulated as is known in the art.

Figure 1D:
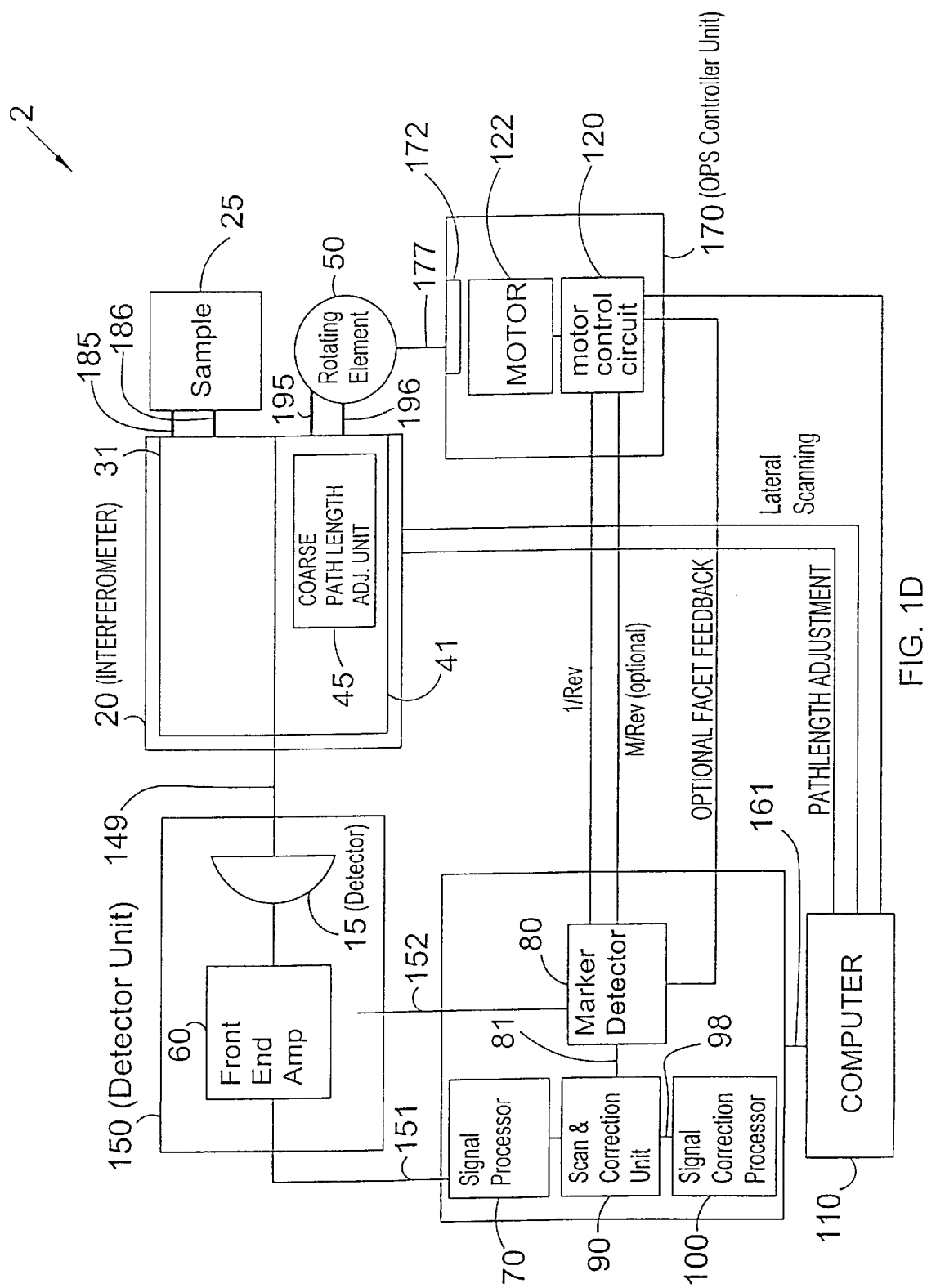
FIG. 1D is a drawing showing another embodiment of an imaging system.

FIG. 1D shows components of an example embodiment OCT system of FIG. 1C in greater detail. The detector unit 150 includes a front end amplifier 60 and a detector 15. The scan analyzer and correction unit 160 includes a first signal processor 70, a marker detector 80, a scan correction unit 90, and a second signal processor 100. Finally, OPS controller 170 includes a sensor 172, a motor control circuit 120, and a motor 122. The system also includes a rotating element 50 as the OPS unit.

The detector 15 receives the interferometric output signal from the interferometer and passes it to the front end amplifier 60 for amplification. The front end amplifier 60 can optionally be coupled to both signal processor 70 via coupling 151, and marker detector 80 via coupling 152. The next element is the scan correction unit 90, and it is coupled to signal processor 70, marker detector 80, and signal processor 100. The marker detector 80 is also coupled to the motor control circuit 120, which in turn is coupled to the motor 122 and the computer 110. Signal processor 100 is also coupled to computer 110. The operation of these components will be described below with reference to specific embodiments. Again, it should be noted that interferometer 20 can include two arms, namely a sample arm (also known as a probe arm) 31 and a reference arm 41, or it can include only one arm which scans both the sample 25 and the OPS unit 175. For simplicity, the descriptions that follow describe an interferometer with distinct arms, although any interferometer could be substituted.

Figure 1E:
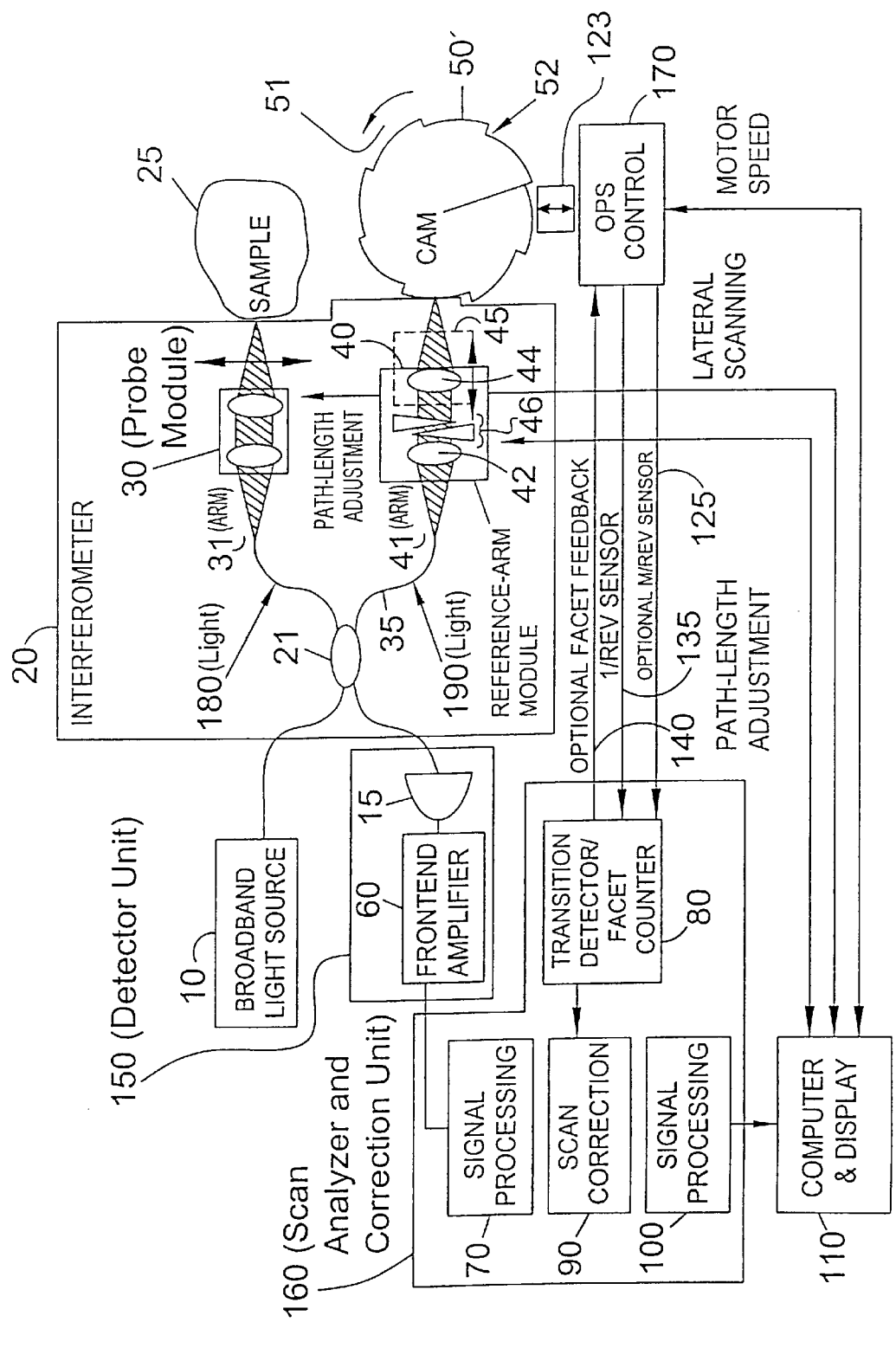
FIG. 1E is a drawing showing an embodiment of an OCT imaging system schematic diagram with a multi-segment CAM.

FIG. 1E shows one embodiment for achieving a high-speed, adjustable-rate longitudinal scanning OCT system 5 according to one embodiment invention. In order to rapidly scan the longitudinal optical reflectivity profile of the sample, the rotating element of this embodiment is a multi-segment CAM 50'. It should be noted that the CAM 50' is used only by way of example, and any rotating element 50 (FIG. 1D) could be substituted into the system.

This embodiment includes a broadband light source 10 which is coupled to an interferometer 20. A simple Michelson interferometer is shown in FIG. 1E, although any other interferometric embodiments can be used, such as the Mach/Zehender, fabryperot, and source or sample-arm referenced interferometers, among others. Also, polarization preserving or polarizing fiber can be used to maintain polarization and polarization discriminating or polarization diversity receivers can be utilized. In this embodiment, the interferometer 20 has a 50/50 single-mode fiber coupler 21 (or splitter) with two output arms, namely a sample arm 31 and a reference arm 41.

The sample arm 31 couples the first portion of split input light 180 into a probe module 30. The probe module 30 has optics to couple light 185 (FIG. 1A) onto the sample 25 and couple light 186 (FIG. 1A) altered by the sample back into the sample arm 31. This embodiment operates in retro-reflected mode, although other embodiments are also possible, such as transmission mode. The probe module 30 also has a one-dimensional or two-dimensional transverse scanning mechanism to scan the light laterally along the sample 25 (as indicated) to produce two-dimensional or three-dimensional images. Alternatively, the sample can be scanned such as in the manufacturing of polymer films in a web inspection application. In that case, the probe is fixed and the sample 25 moves so as to be scanned. Examples of probe modules can include microscopes, catheters, endoscopes, laparoscopes, hand-held probes, probes for injection molding machines, and web inspection machines, among others. The synchronization of the lateral scanning in the probe module 30 with the longitudinal scanning of the reference arm 41 is controlled by a computer 110.

The reference arm fiber 35 leads the second portion of split input light 190 light to a reference arm optical module 40. This module contains optics to couple light 195 (FIG. 1D) from the reference arm to CAM 50'. Specifically, the module focuses light 195 (FIG. 1D) onto CAM 50' using lens 44 of the reference arm module 40. The light is subsequently reflected back into the reference arm fiber 35 as the reference arm return signal 196. As the CAM 50' rotates at a uniform, but selectable speed, the optical path-length is scanned in as uniform a manner as possible so that a constant Doppler shift is approximately achieved, thus simplifying the subsequent signal processing electronics in scan analyzer and correction unit 160. Non-constant Doppler frequency shifts are also possible and can be demodulated as is known in the art. In a later section herein, a family of precise mathematical relationships describing the complex surface 51 of the CAM as a function of a variety of system parameters, such as nominal radius, number of segments, linear scan versus angle, and scan depth, among others, is derived and implemented as part of scan analyzer and correction unit 160.

The reference arm module 40 also has the ability to adjust the path-length by adjusting the distance between two lenses 42, 44 using the coarse path-length adjustment mechanism. Among other benefits, this feature allows for region-of-interest tracking, as will be described in a later section. In this embodiment, the first lens 42 collimates the output of the reference arm fiber 35 and the second lens 44 focuses light onto the surface of the CAM 50'. Since the light is collimated between the two lenses, there is minimal loss in power if the distance between the lenses is adjusted. As discussed earlier, there are alternative path-length adjustment features which could be used.

It is important that dispersion be balanced between the sample arm 31 and reference arm 41. The reference module 40 in the reference arm 41 (or the probe module 30 in the sample arm 31) can contain a prism pair 46 or other suitable devices to match dispersion. Alternatively, with phase synchronous detection at the receiver, dispersion can be compensated for electronically as is known in the art.

The surface 51 of the CAM is such that as the CAM rotates, the distance from the Michelson beam splitter 21 to the surface of the CAM increases linearly. In addition, the surface has a geometry such that the chief ray of a light beam 195 (FIG. 1D) properly targeted on the CAM surface 51 is reflected at a constant angle with respect to the incident light (e.g. retro reflected or reflected toward another target). Note that as the CAM 50' rotates, the optical path-length is scanned in a nearly linear fashion. The CAM surface 51 also has the property that it is optically smooth so that as it is rotated an approximately constant reflectivity is maintained.

The CAM 50' speed is regulated by the OPS unit controller 170, which can use either facet feedback or an inherent sensor, such as an optical encoder or Hall sensor, to regulate speed. Motor control will be discussed in a later section.

One embodiment of the system, as depicted in FIG. 1E, includes a multi-segmented CAM 50' that is driven by a motor 122 (FIG. 1D) similar to that used in polygonal scanners. Note, however, this CAM 50' is quite distinct from the commercial embodiments in use today such as moving mirror embodiments, since the polygon scanners use simple flat mirrors assembled into a polygon, whereas the CAM is a complex surface, as will be described later. The motor is driven and controlled by OPS controller 170. The nominal motor speed can be generated from an on-board clock or can be commanded from the computer 110. The OPS controller has a once-per-revolution (1/Rev) sensor and an optional multiple-pulse-per-revolution (M/Rev) sensor or other suitable means for determining a fixed point(s) on the CAM surface 51. One version of this is unit is optical detector unit 123 which represents a specific embodiment of OPS controller 170. One or both of these sensors, and possibly in combination with a transition detector, keeps track of what facet of the CAM 50' is actively illuminated. Using a pre-computed look-up table or other means, imperfections in the machining of the CAM 50' can be calibrated out in real-time. This can be done using an optical encoder or several other methods as is known in the art including pattern recognition algorithms. Methods of calibration will be discussed in a subsequent section.

Note that the CAM surface 51 can be implemented as illustrated, or for an even number of segments, can have neighboring segments mirror each other. That is, instead of a repetitive low-to-high transitioning, the CAM surface 51 can have low-to-high-to-low transitioning. This can have the added benefits of being easier to machine, having minimal dead-time, and limiting air resistance at high speed since the saw-tooth discontinuity would be eliminated. The trade-off is a modest increase in signal (image) processing complexity.

Region-of-Interest Tracking

Figure 2A:
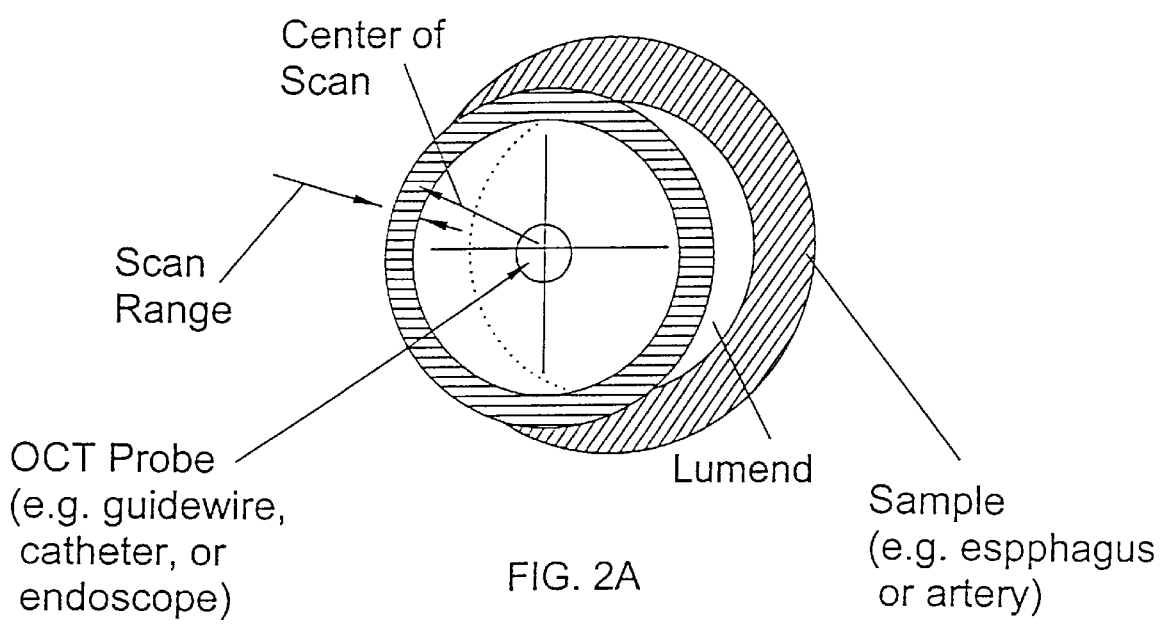
FIG. 2A shows an example of region-of-interest tracking, before the correction, according to another embodiment of the invention.
Figure 2B:
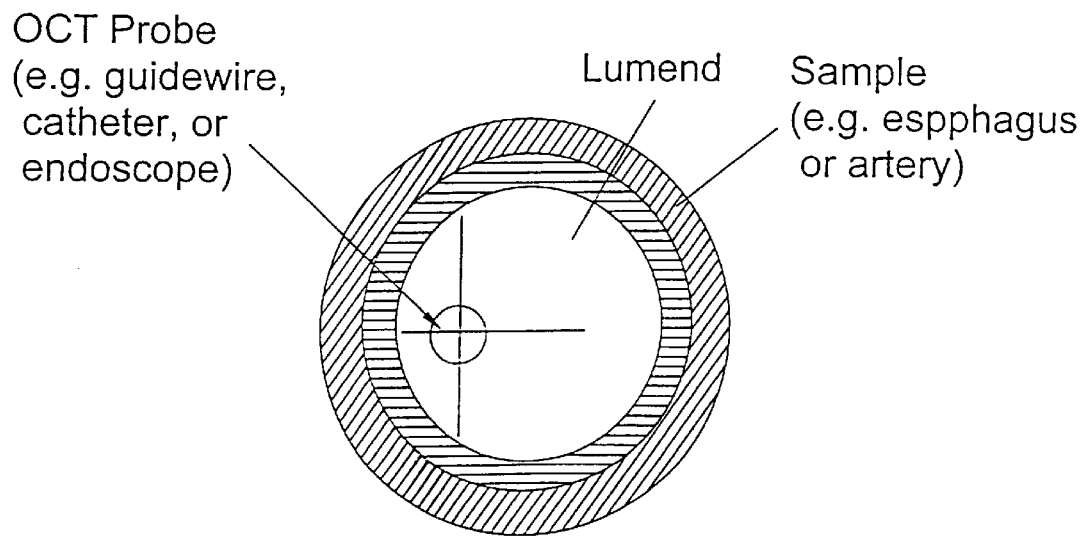
FIG. 2B shows an example of region-of-interest tracking, after the correction, according to another embodiment of the invention.

FIGS. 2A and 2B illustrate region-of-interest tracking for a circumferential scanning system or probe such as may be encountered in a cardiovascular application. Region-of-interest tracking is the positioning of a sample region-of-interest within in the CAM 50' scan depth. As noted previously, any rotating element 50 (FIG. 1D) could be used; CAM 50' is used by way of example. FIG. 2A shows the scan-range, which is the total incremental distance of the longitudinal scan, depicted by the dark black circle which lies between R1 (inner) and R2 (outer), as shown. Thus the center-of-scan is simply the mid-point between R1 and R2. Region-of-interest tracking automatically adjusts the center-of-scan dynamically to keep the scan-range within the region-of-interest within the sample by detecting features such as a vessel wall.

In FIG. 2A, the OCT probe is offset with respect to the region-of-interest to be scanned, which, in this example, is an artery. By dynamically detecting the surface boundary and adjusting the reference arm path-length accordingly, efficiency of the scan can be dramatically improved. FIG. 2B shows an example of region-of-interest tracking after the correction.

Region-of-Interest tracking is important in applications such as catheter/endoscope procedures where the catheter may be offset in the lumen and the scan depth provided by the CAM 50' is not sufficient to cover the offset plus the desired measurement distance into the lumen wall. In FIG. 2A, the scan depth shown would miss the right side of the sample wall and would be penetrating too far into the left side of the sample wall (missing the vessel surface). By using the detection algorithms (e.g. thresholding or other image processing algorithms) for detecting lumen wall, however, the signal correction processor 100 (FIGS. 1A, 1B, 1D) can adjust the coarse path-length adjustment mechanism 45, thereby adjusting the center-of-scan. As the catheter is rotated in the lumen, the distance of the scan within the lumen wall can be kept constant, as illustrated in FIG. 2B. Even in applications where the CAM could be designed to have a wider scan-range, it would not be efficient from a signal-to-noise or acquisition time perspective to image a wider region. Thus region-of-interest tracking can be critically important in OCT systems that have longitudinal scanning mechanisms that can adjust their coarse scan range (e.g. an adjustable scanning optical delay line).

Synchronization

In order to produce OCT images, synchronization of the signal processing and computer display with the rotation of the OPS unit 175 is required. Referring again to FIG. 1A, scan analyzer and correction unit 160 together with OPS unit controller 170 are configured to determine which portion of the OPS unit 175 is undergoing illumination by reference arm signal 195 at any given time. Synchronization can be done in sync master or sync slave mode. In sync slave, OPS unit controller 170 (or the OPS unit 175, for example, CAM 50', in conjunction with the OPS unit controller 170) is the master clock and the computer 110 (processor) synchronizes (e.g. its horizontal scan rate) to the OPS unit 175. In sync master, the OPS controller unit 170 or the motor control circuitry 120 (FIG. 1D) synchronizes to a clock provided by the computer 110. In either case, it is preferable that the machining and OPS unit system imperfections be calibrated in real-time to obtain high resolution images. Methods for this will be discussed below.

There are several methods available to achieve synchronization. All of the methods use information from the OPS unit 175, OPS unit controller 170, and/or rotating element 50 (FIG. 1D) in some way, either by using the inherent geometry of the OPS unit, or by using an external sensor, such as the optical detector unit 123 or the OPS sensor 172 (FIGS. 1E and 1B), in combination with OPS unit 175 modified so as to trigger the sensor. The discussion that follows is drawn primarily to synchronization of the specific embodiment of a CAM as an OPS unit 175, as shown in FIG. 1E. It should be understood that synchronization can be achieved in analogous manners for any of the specific OPS units discussed, or others known in the art.

The simplest but least effective method to synchronize uses a segmented CAM 50', and takes advantage of the drop in back-reflected light power at the segment transitions 52 of the CAM 50'. The power drop is inherent to the geometry of the CAM 50'.

Figure 3:
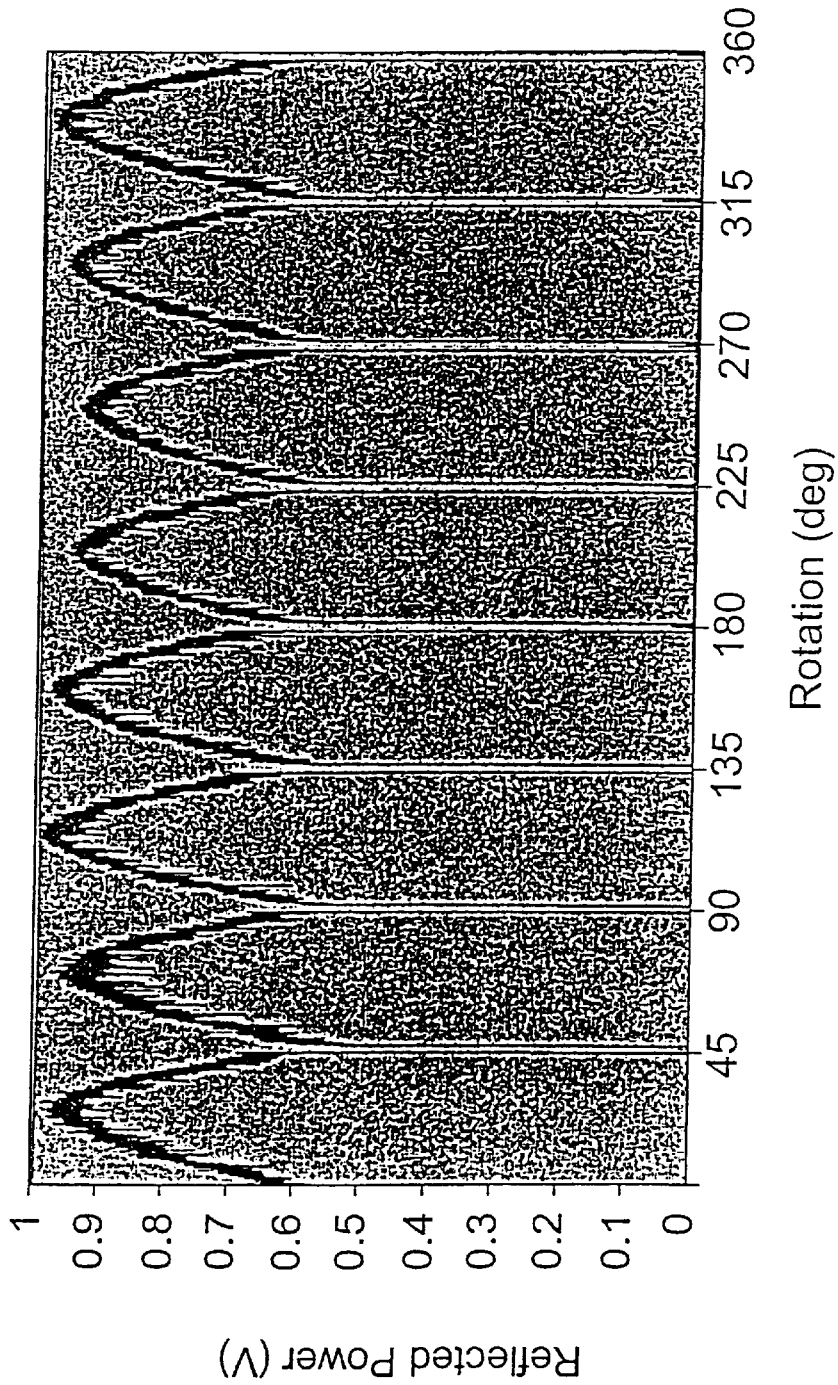
FIG. 3 shows the measured reflectivity profile of an eight segment CAM, according to another embodiment of the invention.

FIG. 3 shows the measured back-reflected power as a function of rotation angle for a 8 segment CAM 50' (similar to that described later). In a preferred embodiment, the depth-of-field of the CAM focusing lens 44 should be approximately equal to or greater than the scanning range of the CAM 50' to minimize variation in power reflections as the CAM is rotated. A longer depth-of-field results in a larger focused spot on the CAM surface 51. This causes less power fluctuations due to focus errors, and more tolerance to small machining marks. A larger focus spot, however, leads to more sensitivity to non-ideal tilt of the surface and larger machining imperfections. It also leads to a lower duty cycle since it takes a greater percentage of a full revolution to fully transition across a segment boundary 52 of the CAM 50'.

In the measurement shown in FIG. 3, the confocal parameter was approximately 5 mm and the longitudinal scanning range of the CAM was approximately 4 mm and the CAM was spinning at 250 rotations-per-second. Note that within each segment the (normalized) reflected power starts at ~60% (since the CAM surface is out-of-focus), increases to ~100% in the center of the segment (when the surface is in focus), and then decreases again to ~60%. Then there is an abrupt loss of power as the focused beam transitions over a segment boundary 52. It is the detection of this loss of power that can be used for segment triggering, as discussed below. Note that if a longer confocal parameter is used (e.g. 8 mm), the power fluctuations within each segment will be lower, but higher tilt stability is required. In this example, the light was focused near the surface of the CAM using spherical optics. Cylindrical focusing can also be used to yield higher efficiency. Also, the light can be focused (using cylindrical or spherical lenses) closer to the center of the CAM facet radius of curvature to yield better mode-matching efficiency.

Other synchronization methods can achieve greater accuracy, and are discussed below.

Synchronization Using Front-End Amplifier as Transition Detector and 1/Rev Sensor In one embodiment, synchronization of the CAM 50' is accomplished by sensing the short pulses (or blanking) present in the DC photocurrent. These pulses are first detected in the front-end amplifier 60 as the light focused on the CAM 50' transitions over the segment boundaries 52 and is temporarily not retro-reflected. Each of the pulses causes the triggering for each segment.

Figure 4:
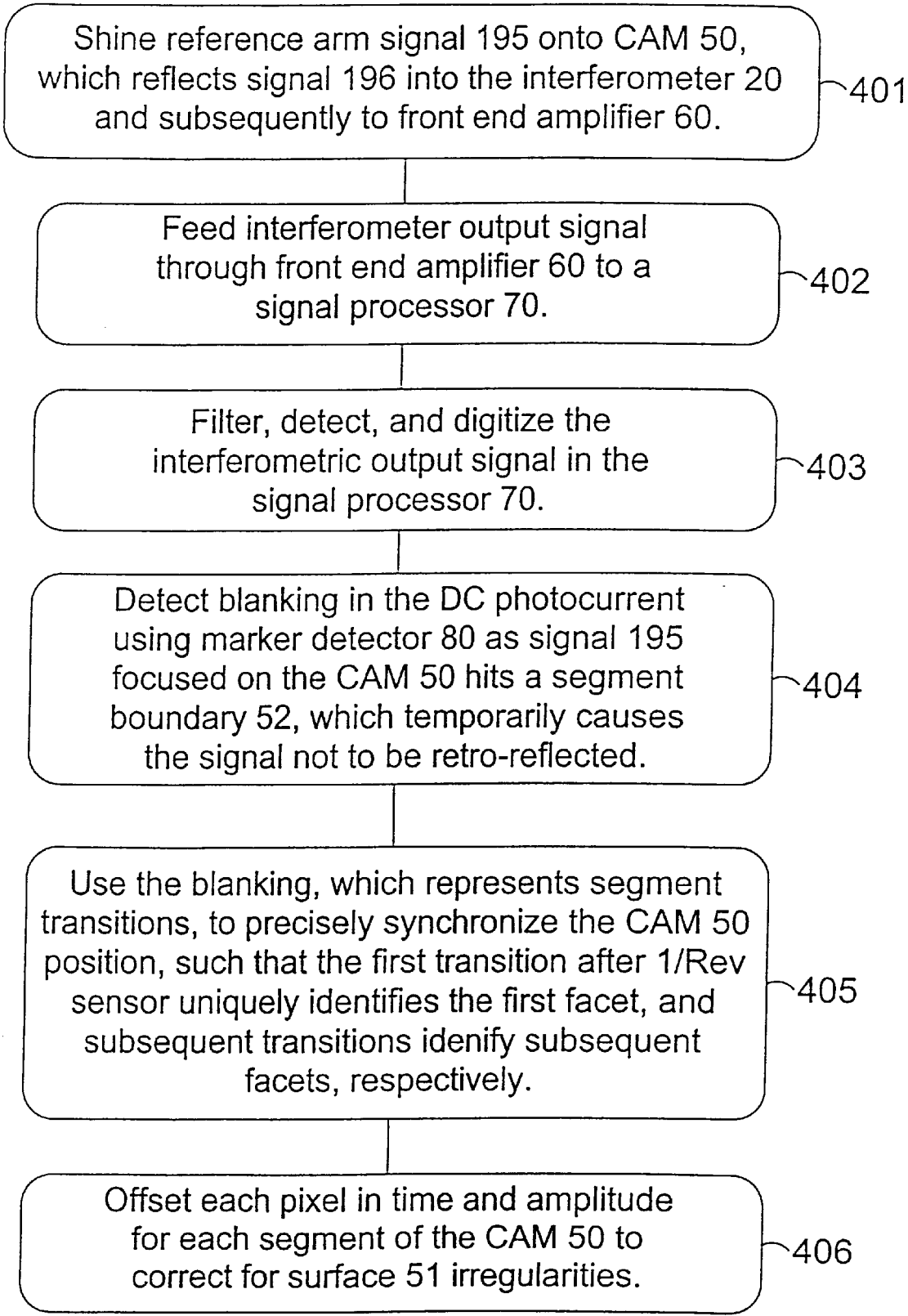
FIG. 4 shows a method of synchronization using the once-per-revolution (1/Rev) sensor in combination with the marker detector to perform tracking of which facet of the CAM is actively undergoing illumination by the OCT light, according to one embodiment of the invention.

A method of synchronization according to one embodiment as shown in FIG. 4, with reference to FIGS. 1A and 1E. The method includes step 401, which calls for shining reference arm signal 195 onto CAM 50', which reflects the signal 196 into the interferometer 20 and subsequently to front end amplifier 60. Next, step 402 includes feeding the interferometer output signal through front end amplifier 60 to a signal processor 70. Then, in step 403, the interferometer output signal is filtered, detected, and digitized in the signal processor 70. Step 404 detects blanking in the DC photocurrent using marker detector 80 as light focused on the CAM 50' hits a segment boundary 52, which temporarily causes the light not to be retro-reflected. Step 405 follows, and includes using the blanking, which represents segment transitions, to precisely synchronize the CAM 50' position, such that the first transition after the 1/Rev sensor uniquely identifies the first facet, and each subsequent blanking signal identifies subsequent facets. Finally, step 406 includes offsetting each pixel in time for each segment of the CAM 50' so as to correct for a surface 51 irregularities.

This method of synchronization relies on the use of the once-per-revolution (1/Rev) sensor in combination with marker detector 80 (FIG. 1A) to perform tracking of the particular facet of the CAM 50' actively undergoing illumination by the OCT light. The 1/Rev sensor can be any type of sensor, including optical, electromagnetic, magnetic, electronic, capacitive, mechanical, or any other type known in the art. In one embodiment, the sensor is an optical interrupt switch, such as an LED, positioned normal to the CAM surface 51. It senses a previously placed mark on the CAM surface 51 which uniquely identifies the position of CAM 50'. As CAM 50' moves in a cyclic fashion, the mark passes over the sensor thereby triggering it. When the sensor is triggered, it identifies the position of the CAM for a given point in time. Again, it should be understood that the same technique can be used for any given OPS unit.

The function of the 1/Rev sensor can also be accomplished without the need for a 1/Rev sensor or detector. By making one of the segment boundaries 52 of the CAM 50' unique, for instance not as steep, the drop in power as shown in FIG. 3 over that unique boundary will be different than the other segment transitions. The scan analyzer and correction unit 160 can detect this difference and use that information to synchronize the system. This technique can be used with any rotating element 50 in place of or in addition to the 1/Rev sensor.

This type of segment tracking, in combination with prior calibration of the CAM system imperfections, allows the scan to be corrected. In one embodiment, the front-end amplifier 60 feeds the signal processor 70 that filters and detects and digitizes the interferometric signal. As the reference arm signal 195 passes over a CAM segment transition 52, there is an abrupt loss of power (as was illustrated in FIG. 3) that can be used to precisely synchronize the CAM position. For example, the first CAM transition after the 1/Rev sensor uniquely identifies facet number one. For each segment of the CAM, each pixel can be offset in time (or equivalently sample depth) and amplitude to correct for surface irregularities in the scan correction block.

In many instances, it is necessary to correct for slope and offset, and the correction algorithm is a simple linear operation. In other instances, it is only necessary to correct for offset. Thus one algorithm is simple: place a predetermined number of blank pixels at the start of each segment to fill-in for the appropriate offset. This approach, however, can potentially be corrupted by large signals from the sample "blinding" the front end amplifier 60. Blinding is caused by large sample reflections which saturate the photodetector 15, which in turn implies that the power drops in the reference arm can no longer be detected. One method to eliminate this problem is to place a separate sensor 172 (FIGS. 1D, 1E) in the OCT. Other methods are described next.

Synchronization Using 1/Rev and M/Rev Sensor

Another method of synchronization uses two sensors from the OPS unit 175, namely the 1/Rev sensor and the M/Rev sensor (where M is the number of facets). The M/Rev sensor is targeted at the edges of the OPS unit or other suitably marked sections of the OPS unit so that each facet has a triggering signal. This approach has the advantage that large signals from the sample will not "blind" marker detector 80.

Figure 5:
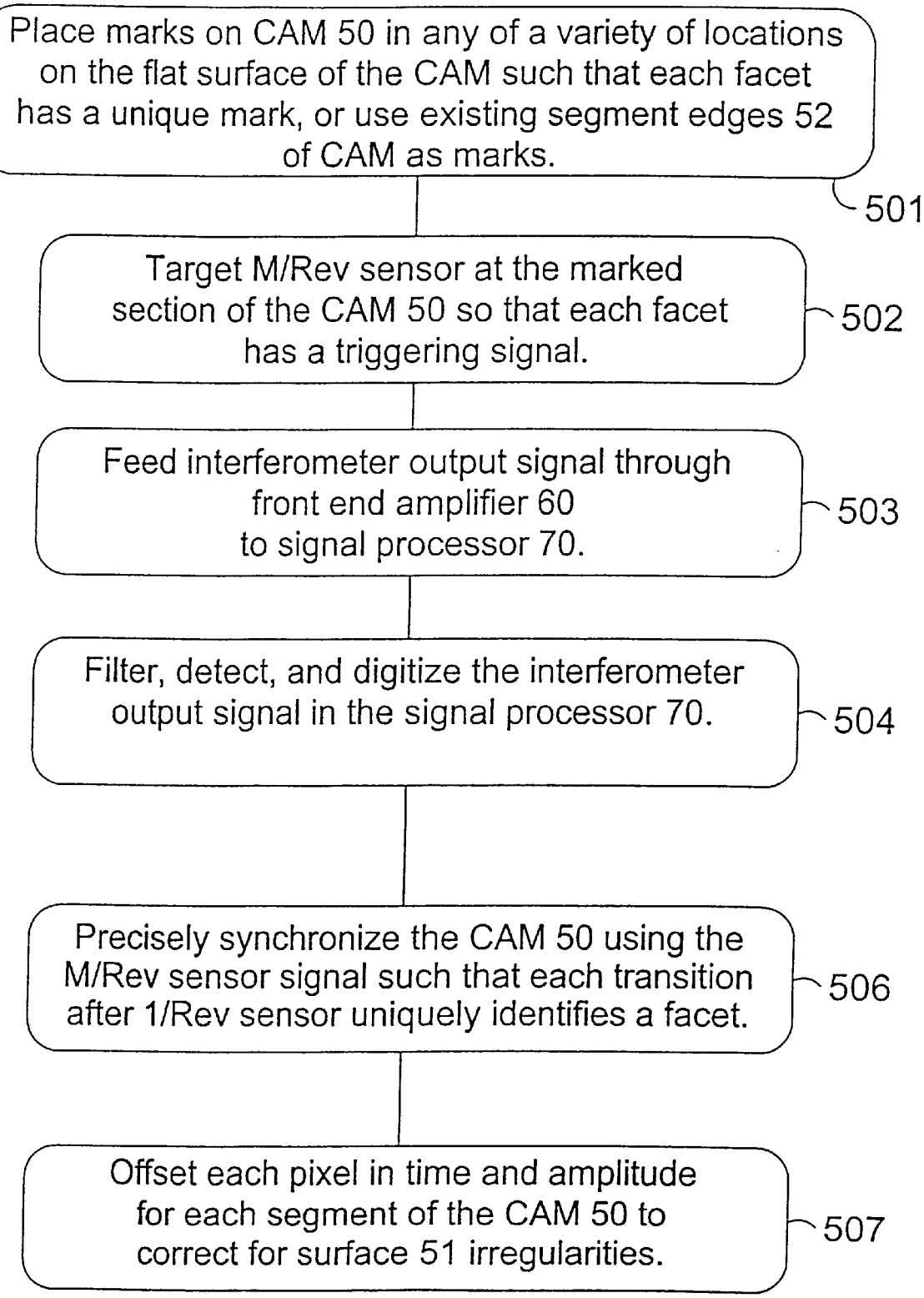
FIG. 5 shows a method for synchronization of the system using 1/Rev and M/Rev sensor, according to one embodiment of the invention.

A method of synchronization according to a preferred embodiment is shown in FIG. 5, with reference to FIGS. 1A and 1E. This method includes step 501, where marks are placed on CAM 50' in any of a variety of locations on any flat surface of the CAM such that each facet has a unique mark. Alternatively, the existing segment edges 52 of the CAM 50' can be used as segment markers. Next, step 502 includes targeting the M/Rev sensor at the marked section of the CAM 50' so that each facet has a triggering signal. Step 503 follows, and includes feeding interferomic output signal through front end amplifier 60 to signal processor 70. Signal processor 70 then filters, detects and digitizes the interferomic output signal, according to step 504. Next, according to step 506, the CAM 50' is precisely synchronized using the M/Rev sensor signal such that each transition after 1/Rev sensor uniquely identifies a facet. Finally, step 507 calls for offsetting each pixel in time and amplitude for each segment of the CAM 50' to correct for surface 51 irregularities.

Thus, according to this method, marks (e.g. lines scribed, painted, or bonded) are made on the OPS unit 175. The marks can be placed in a variety of locations such as on the flat surface (top, bottom, or side) of the OPS unit 175, and indicate the OPS unit position when read by a sensor 172 (FIG. 1B) (e.g. optical, mechanical, electromagnetic, etc.). Additionally, it is possible to use the existing and inherent segment edges 52 on the CAM 50' or other inherent segment boundaries of any rotating element 50. Thus, the scan analyzer and correction unit 160 can perform the detection. Also, as noted previously, one segment transition can be unique, so as to allow the scan analyzer and correction unit 160 to perform the function of the 1/Rev sensor.

The M/Rev detection method works on the same principle as the 1/Rev sensor, but is calibrated to each facet. In some manufacturing embodiments, it is simpler and more robust to mark a surface (or even place a plastic sticker on the surface and mark the sticker) than to machine trim and precisely mount the OPS unit to the motor shaft. Such marking is effective in solving problems with triggering if the position errors are deterministic. It should be noted that this procedure can be implemented with or without an optical transition detector. Thus when both the 1/Rev and M/Rev sensors are implemented, there is no need for optical feedback from the interferometer; all of the synchronization information is established using the markings, and the respective 1/Rev and M/rev sensors.

Synchronization Using Only 1/Rev Sensor

Figure 6:
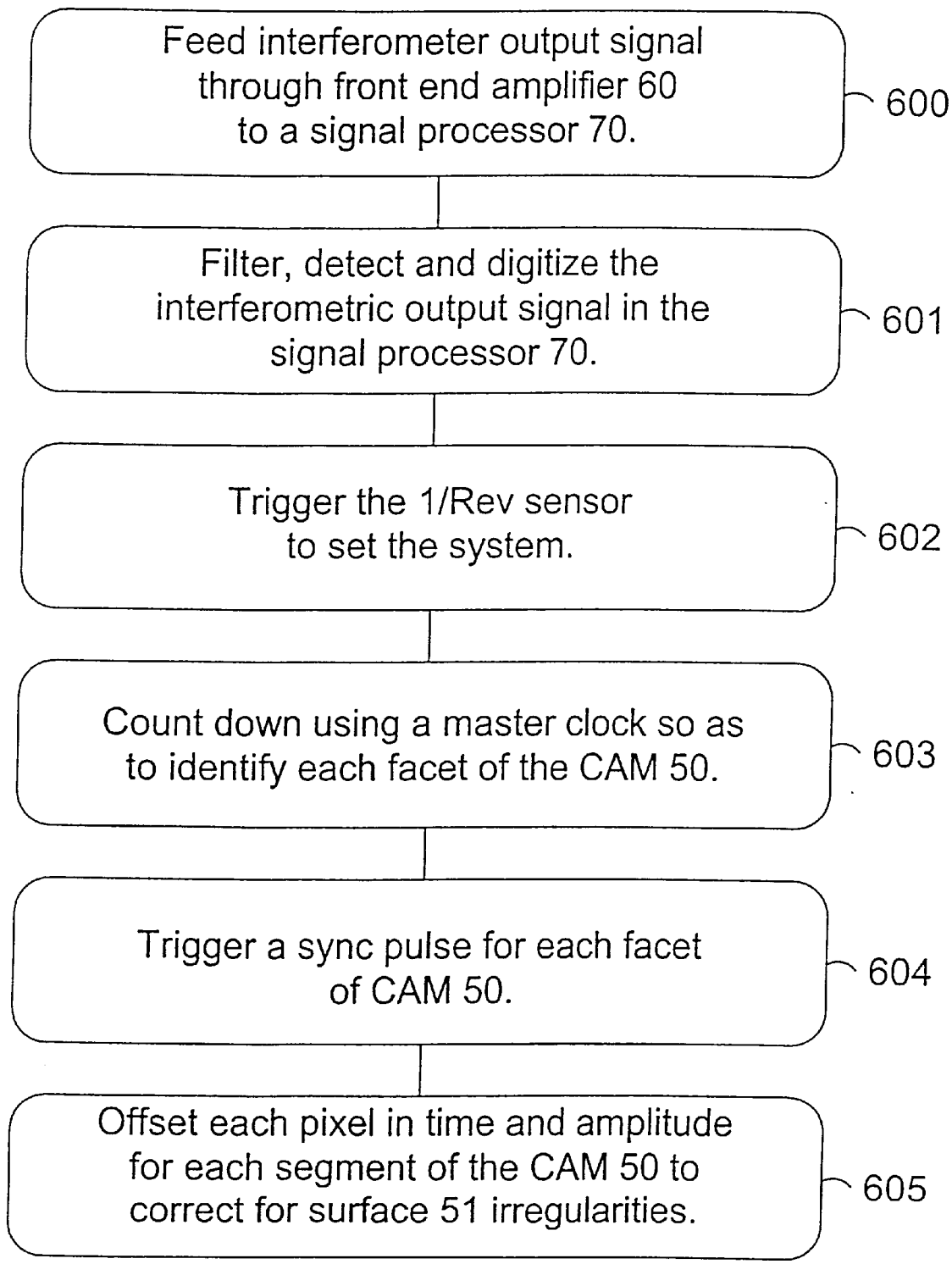
FIG. 6 shows a method of synchronization using only 1/Rev sensor, according to one embodiment of the invention.

Referring to FIG. 6, in another embodiment, the velocity variations are relatively constant within one revolution of the OPS unit. In such a scenario it is possible to use only the 1/Rev sensor. Where the OPS unit 175 is a CAM, each segment of the CAM is identified by counting down from a master clock starting from the 1/Rev sensor. For example, if there are eight facets, then there are eight values which the counting circuit uses to trigger a sync pulse. This approach has the advantage of being the lowest cost, and does not suffer from potential sync dropouts due to large sample arm reflections.

Thus, referring to FIGS. 6 and 1E, interferomic output signal is fed through front end amplifier 60 to signal processor 70, according to step 600. Signal processor 70 then filters, detects and digitizes the interferomic output signal, according to step 601. The 1/Rev sensor is triggered to set the system, as shown in step 602. Next, as shown in step 603, a master clock counts down to identify each facet of the CAM 50'. In step 604, a sync pulse is triggered for each facet of the CAM 50'. Then, according to step 605, each pixel is offset in time for each segment of the CAM 50' to correct for surface 51 irregularities.

Calibration

The discussion that follows is drawn primarily to calibration of the specific embodiment of a CAM 50' as an OPS unit 175. It should be understood that calibration can be achieved in analogous manners for any of the specific OPS units discussed, or others known in the art.

In many instances it is difficult to machine the CAM 50' to an accuracy of less than the coherence length of the source. This can be due to imperfections in the beginning of each CAM segment (e.g. segment boundaries are not exactly 45 degrees for an eight (8) segment CAM) or imperfections along the radius 53 of the CAM. Further, when the CAM 50' is mounted on the motor shaft off center (eccentricity), there can be a systematic position error of each CAM facet as a function of rotation. The mounting of the CAM is highly sensitive because the position error of the rotation axis results in a position error which is two times larger. Thus if the rotation axis of the CAM is off center by 5 $\mu$m, the total error will be 10 $\mu$m because one facet will be too close to the center by 5 $\mu$m, while the opposite facet will be too far from the center by 5 $\mu$m. As a result, many CAM manufacturing techniques will require calibration after mounting on the motor shaft.

In these and other instances, the quality of the OCT image is degraded in proportion to the machining or alignment errors. Other calibration errors include effects of imperfect CAM/motor control loops. As is evident from many motors that have been tested, imperfection in the motor control loop leads to random or periodic velocity imperfections. Thus if the CAM 50' is driven in sync master mode, there will be timing errors that lead to position errors which cause the OCT image resolution to be degraded.

If the CAM 50' is driven at a constant angular velocity, the path-length variations will be repetitive and linearly varying in time. The synchronization of the image data and/or the control of the velocity can be derived by detecting the loss in power of the retro-reflected signal as the light beam traverses the segment boundaries 52 of the CAM 50', as shown in FIG. 3, or by other methods such as were described above. Due to limitations in the ability to precision-manufacture the CAM surface 51, there can be slight path-length changes between each segment surface of the CAM. This can severely reduce the imaging ability or resolution of the OCT system. If the surface is calibrated, however, the imperfections in the surface can be corrected in real-time when the appropriate synchronization circuitry or system is implemented as previously described.

Depending on the quality of the finish on the CAM surface 51 and its mounting and motor assembly and control loop, it is necessary that the CAM surface 51 be calibrated using a calibration technique and stored permanently in a look-up table (or other means) so that the image quality can be restored. This look-up table would be used, in real-time (or non real-time), to calibrate out any surface irregularities using post detection re-registration.

Figure 7A:
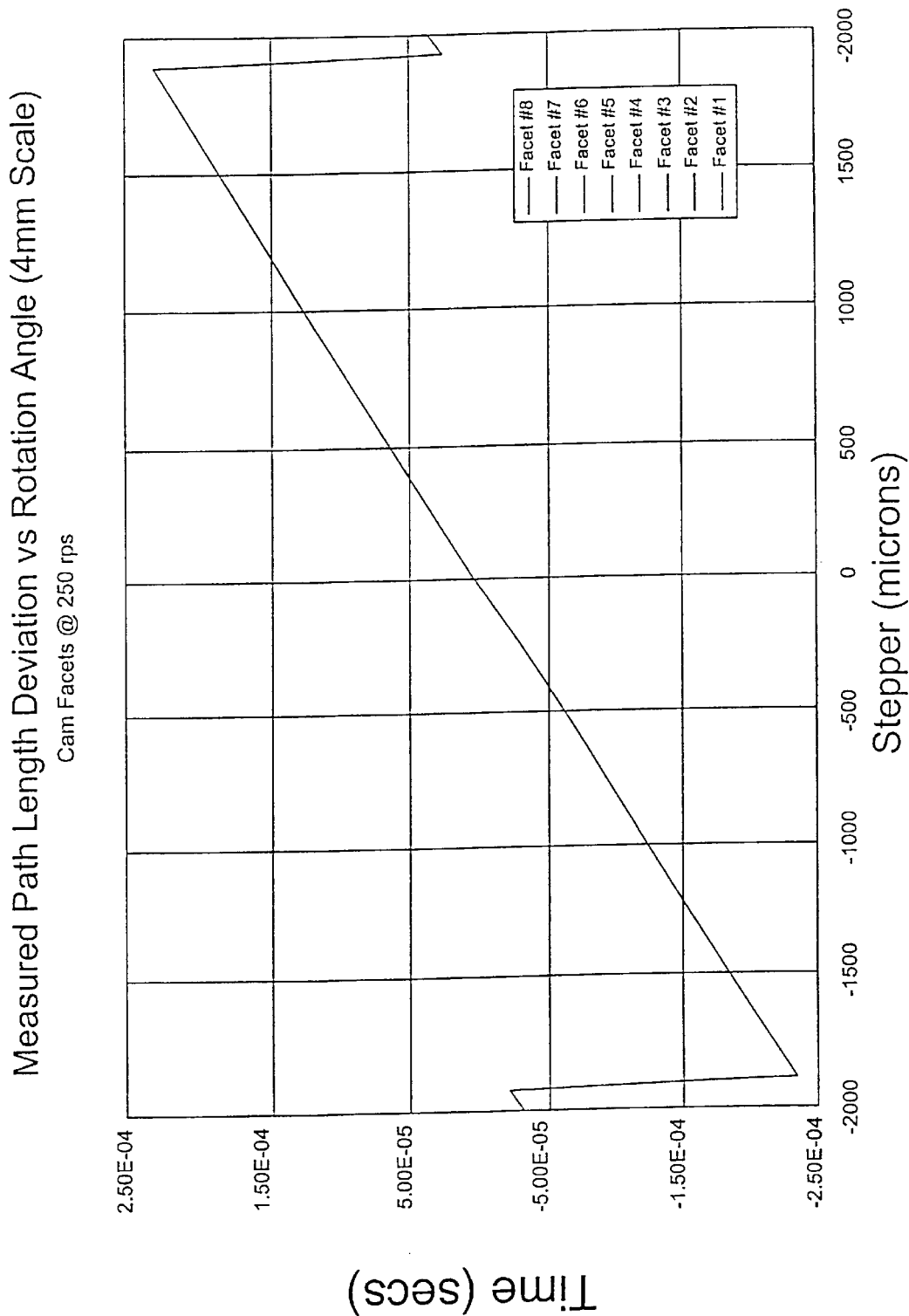
FIG. 7A shows the measured timing (or equivalently path-length) variation of an embodiment of an 8-segment CAM versus the position of a stepper motor on a 4 mm scale.
Figure 7B:
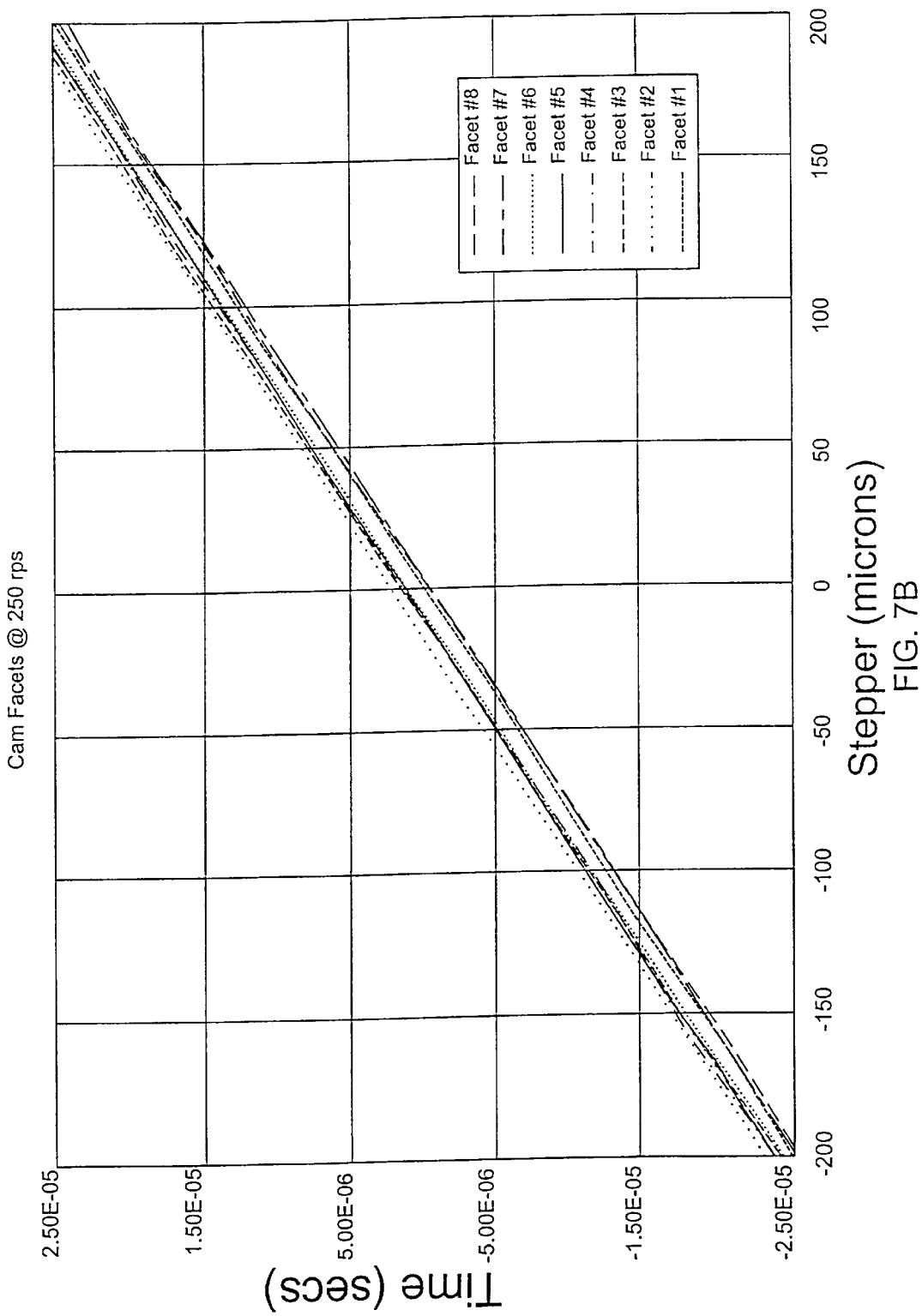
FIG. 7B shows the measured timing (or equivalently path-length) variation of an embodiment of an 8-segment CAM versus the position of a stepper motor on a 400 $\mu$m scale.

FIGS. 7A and 7B show the measured timing (or equivalently path-length) variation of a preferred embodiment of the eight segment CAM versus the position of a stepper motor on a 4 mm and 400 µm scale respectively. Note that the slopes of the eight segments are very similar but, as seen in FIG. 7B, there is an offset variation equivalent to about 10 to 20 µm. This illustrates the CAM 50' is very linear versus rotation angle and that there are slight imperfections from segment to segment that need to be calibrated for proper use of the CAM 50' in an OCT system. By storing the required offset to make all eight of these curves overlap in a look-up-table and applying this offset by inserting a varying number of blank pixels in the scan correction block, accuracy can be restored to the OCT image. This calibration need only be done once at the factory or can be done in an automated fashion in the field. Other calibration techniques besides a precision stepper motor can also be used.

Figure 8:
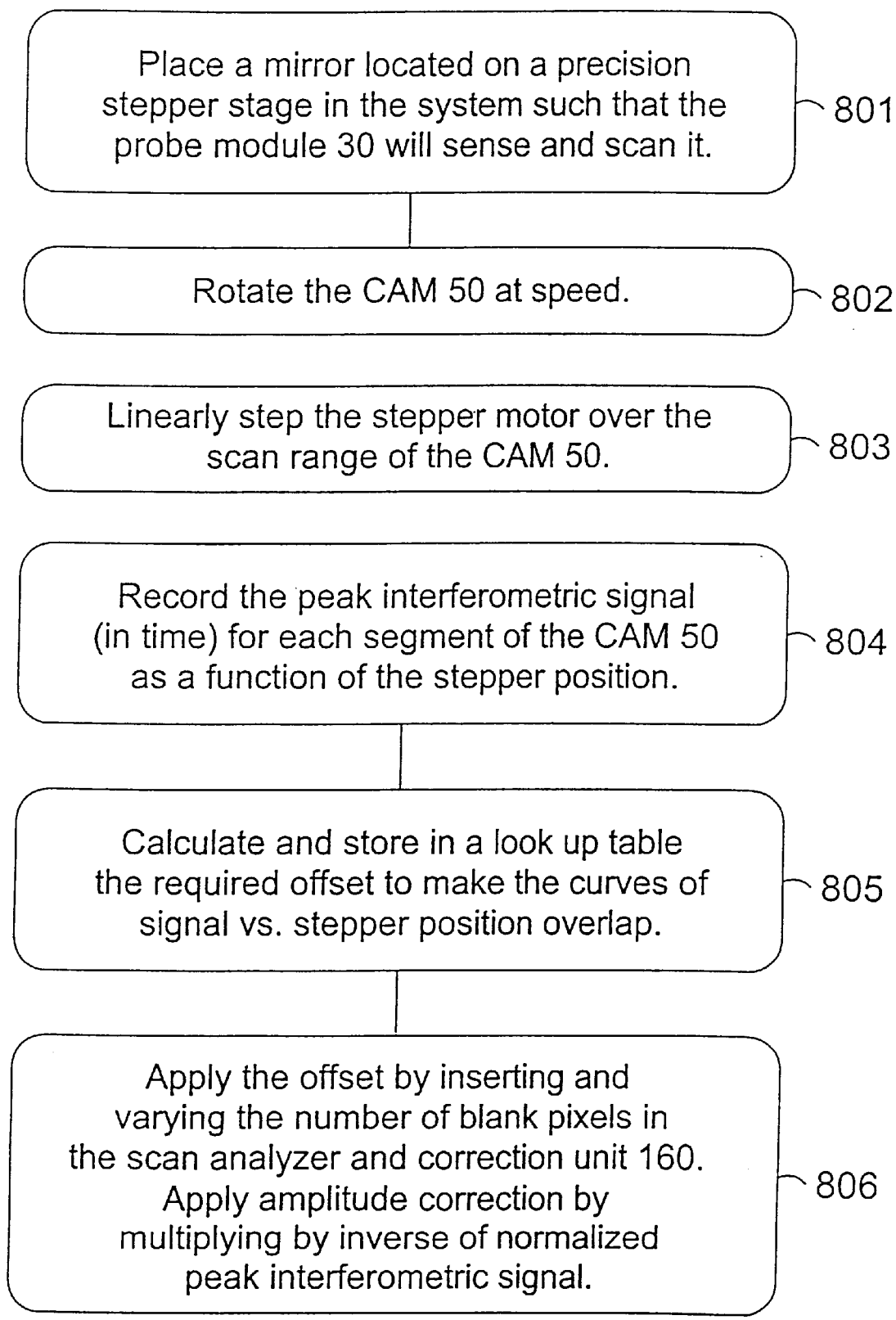
FIG. 8 illustrates a method for calibrating the Optical Path-length Scanning Unit by using mirror located on a precision stepper stage, according to one embodiment of the invention.

A method of calibration according to one embodiment is shown in FIG. 8, with reference to FIG. 1E. The method includes step 801, which calls for placing a mirror located on a precision stepper stage in the system such that the probe module 30 will sense and scan it. Next, CAM 50' is rotated at speed, according to step 802. Step 803 includes linearly stepping the stepper motor over the scan range of the CAM 50'. Then, in step 804, the peak interferomic signal in time is recorded for each segment of the CAM 50' as a function of the stepper position. Step 805 then requires calculating and storing of the required offset to make the curves of the signal versus stepper position overlap. Finally, step 806 calls for applying the offset by inserting and varying the number of blank pixels or delaying a trigger pulse in the scan analyzer and correction unit 160. Also, the amplitude can be corrected by multiplying the recorded pulses by the inverse of the peak interferometric signal.

This method for calibrating the CAM surface, as shown in FIG. 8, is further described as follows. A mirror located on a precision stepper stage is used in place of the sample 25. The CAM 50' is then rotated at speed and the stepper motor is linearly stepped over the scan range of the CAM 50'. For each segment of the CAM, the peak interferometric signal (in time) can be recorded as a function of stepper position. This technique was used for an eight segment CAM, the details of which are described in a subsequent section.

Figure 9:
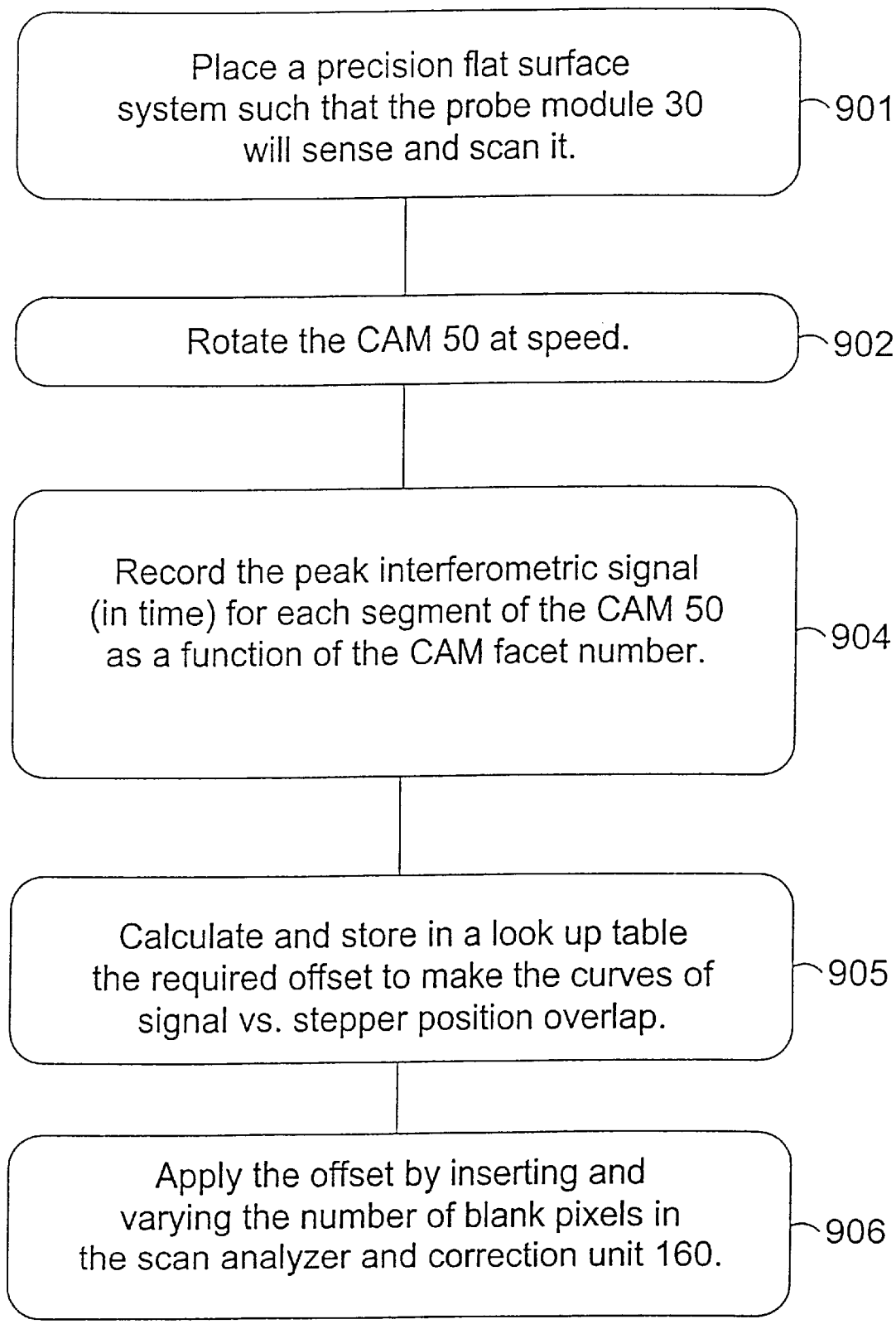
FIG. 9 shows a method of a calibration using a precision flat surface, according to one embodiment of the invention.

Referring to FIG. 9, where offset is the only concern, a precision flat surface can be scanned. The image of that scan is acquired and stored, and using a line-to-line cross correlation algorithm, the CAM offsets can be calculated and stored in a look-up table.

Thus, a method of calibration according to one embodiment is shown in FIG. 9, with reference to FIG. 1E. This method includes step 901, placing a precision flat surface in the system such that the probe module 30 will sense and scan it. Preferably, this flat surface is placed nominally in the center of the scan region. Next, according to step 902, CAM 50' is rotated at speed. Then, for each segment of CAM 50', the peak interferometric signal for each longitudinal scan in time is recorded as a function of the CAM facet number, as recited in step 904. In this case, one peak will be recorded for each facet. The peak corresponds to the point in time when the facet position and the precision flat surface are matched in optical path-length. Only one peak will be recorded for each facet. Step 905 calls for calculation and storage of the required offset to make the curves of the signal versus stepper position overlap. Finally, in step 906, the offset is applied by inserting and varying the number of blank pixels in the scan analyzer and correction unit 160.

Figure 10:
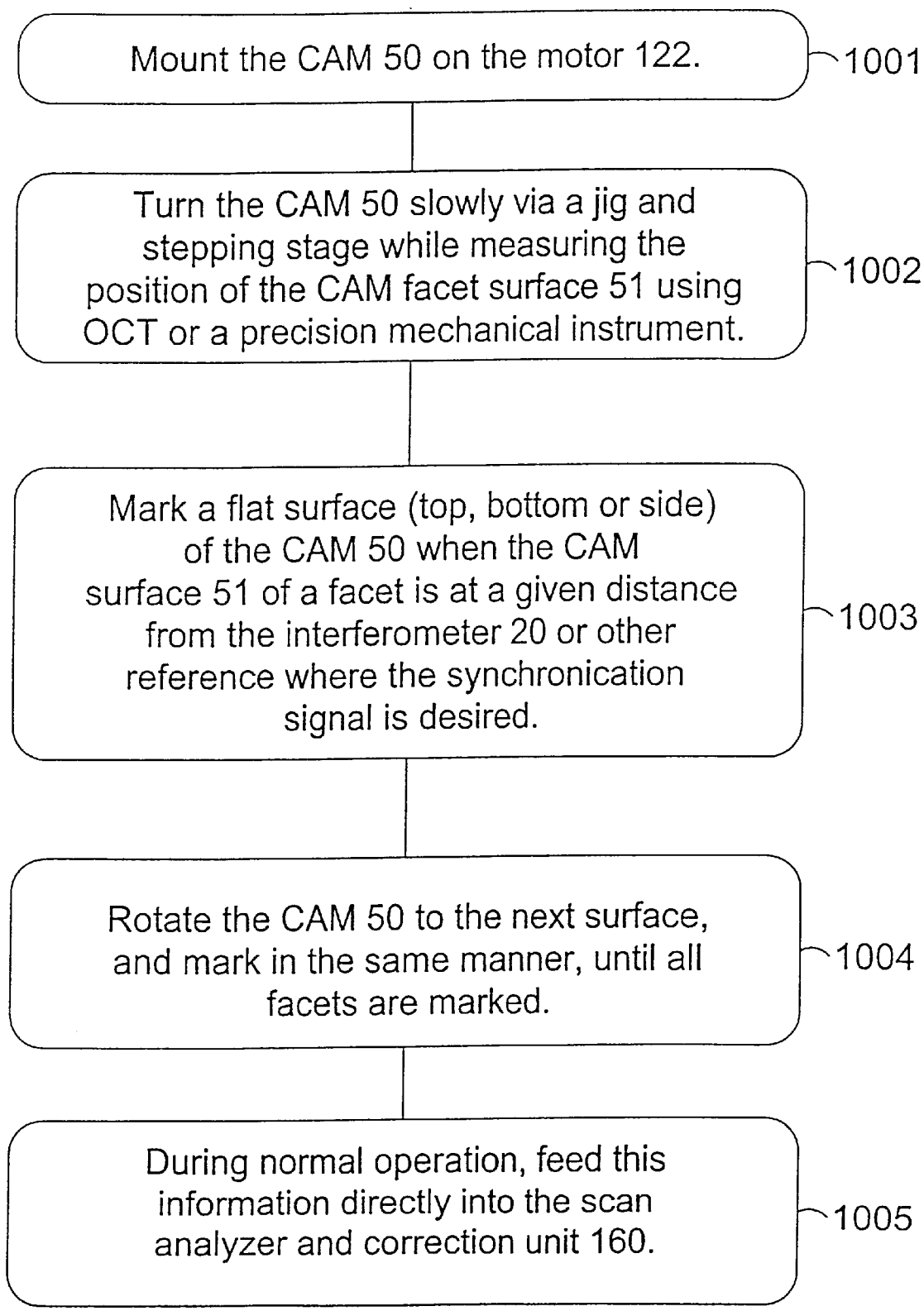
FIG. 10 shows a method of calibration which eliminates the need for the OCT scan correction and signal scan correction processing mechanism, according to one embodiment of the invention.

Referring to FIG. 10, there is another class of CAM scanning mechanism imperfections that can be calibrated in a way that eliminates the need for the OCT scan correction and signal processing mechanism to re-register the OCT image. Thus, in an embodiment where only offset correction is needed, it is possible to eliminate the need for the transition detector and scan correction processing. Using, for example, the marking of the top or bottom surface of the CAM described above and precisely placing the marks with respect to the CAM segment transitions 52 and CAM radius 53, all the calibration is effectively embedded into the scan triggering mechanism and can be fed directly into the signal correction processor 100 (FIG. 1A) without any need for further processing.

Referring to FIGS. 10 and 1A–1E, to implement these marks or fiducials, the CAM 50' can be mounted on the motor 122, according to step 1001, and turned slowly via a jig and stepping stage (not shown) while measuring the position of the CAM facet surface 51 using OCT or a commonly available precision mechanical surface measurement instrument, as shown in step 1002. Next, according to step 1003, when the CAM facet surface is at a given distance from the interferometer 20 or other reference where the synchronization signal is desired, the flat (top, bottom, or side) surface of the CAM 50' is marked (e.g. scribed or painted) using a jig which marks repeatedly. Step 1004 then requires that CAM 50' be rotated to the next facet and the process repeated. This yields marks which are calibrated to each facet distance. Because the facet distance for a preferred embodiment of the CAM changes about 4 times more slowly than the arc length at the outer boundary of the CAM, the accuracy of the scan position will be 4 times higher than the accuracy of the marking. Finally, according to step 1005, the information from the previous steps is fed directly to the scan analyzer and correction unit 160 during normal operation.

The forgoing discussion illustrates examples of how to correct for scan mechanism imperfections, which is a requirement for high-resolution OCT systems. Numerous other methods can also be implemented. Although many of the examples explained the process in terms of a CAM, it should be understood that such techniques can be applied to any given OPS unit.

Figure 11:
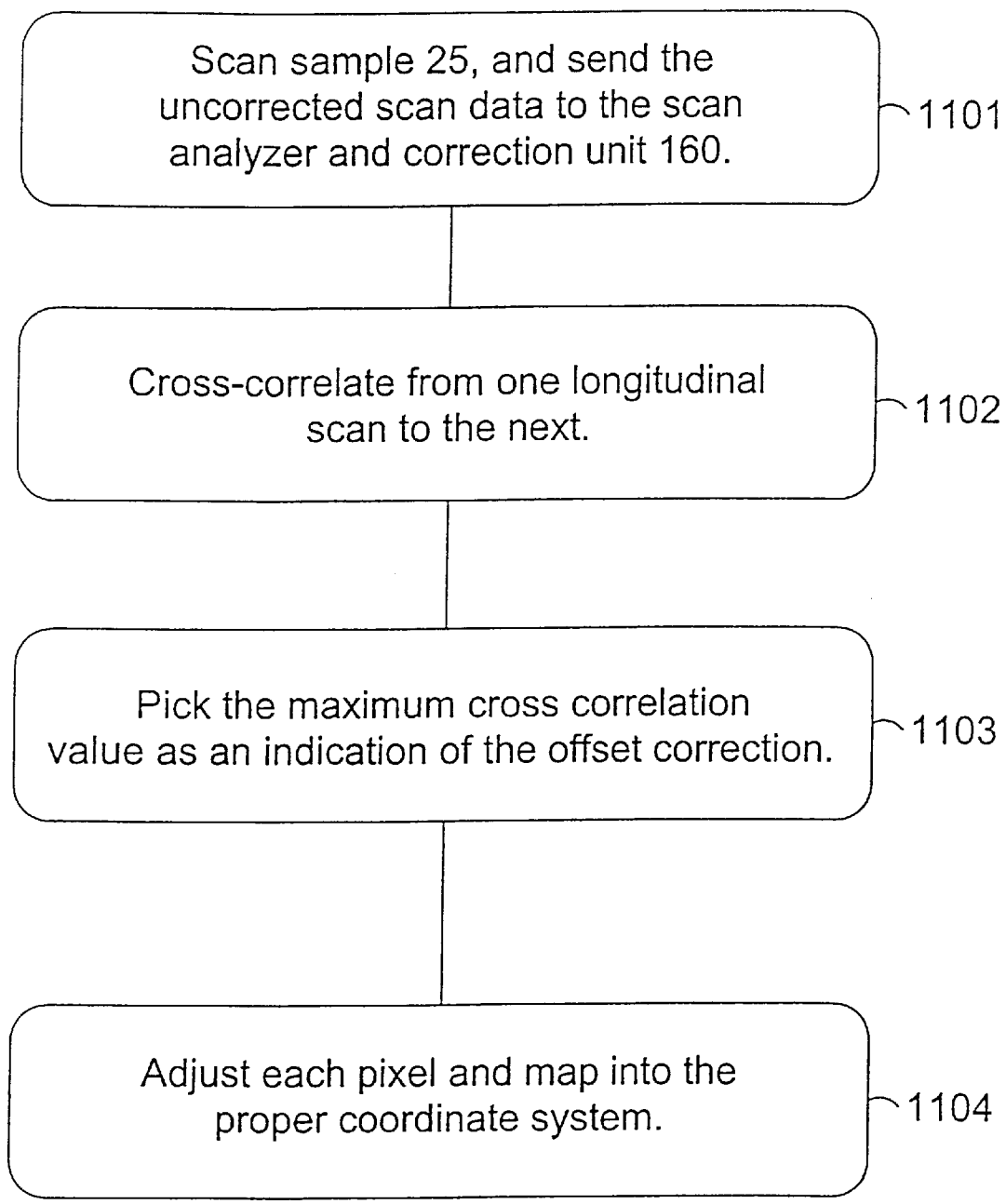
FIG. 11 shows a method of calibration using signal processing techniques that cross-correlate from one longitudinal scan to the next and pick the maximum cross-correlation value as an indication of the offset correction, according to one embodiment of the invention.

Referring to FIG. 11, for example, another method for calibration according to one embodiment of the invention is to use signal processing techniques that cross-correlate from one longitudinal scan to the next and pick the maximum cross-correlation value as an indication of the offset correction. This is similar to the procedure depicted in FIG. 9, but the actual sample, rather than a mirror or a precision flat surface, is used as a reference. As stated above, every pixel can be adjusted and mapped into the proper coordinate system. One important feature of this aspect of the invention is that when OPS unit imperfections are calibrated, there is a means to track which section of the OPS unit is undergoing illumination. This can be done using a marker detector 80, a M/Rev sensor, and a 1/Rev sensor, or combination thereof, or equivalent methods, and using a scan correction process to calibrate the scanning imperfections out in real-time. Such a method allows an OCT image of high resolution to be displayed or stored.

Thus, a method of calibration according to one embodiment is shown in FIG. 11, with reference to FIG. 1E. This method includes step 1101, whereby sample 25 is scanned, preferably repeatedly in the same spot, and the uncorrected scanned data is sent to the scan analyzer and correction unit 160. Next, in step 1102, the data is cross-correlated from one longitudinal scan to the next. Step 1103 then calls for picking the maximum cross-correlation value as an indication of the offset correction. Finally, in step 1104, each pixel is adjusted and mapped into the proper coordinate system.

CAM Manufacturing

There are a variety of methods to manufacture the CAM. They include, first, using a multi-axis diamond turning machine; second, vapor-polishing and/or applying a thick metal overcoat to a precision (0.0005") jig ground base; third, bonding thin flexible metal mirrors to a precision base; and fourth, utilizing mechanical polishing techniques for a precision base. Moreover, there are other methods known in the art which can also be used. One additional example is to bond micro retro-reflectors to a machined CAM surface. Once a master is fabricated, it is possible to manufacture CAMs to the necessary tolerance using injection molding techniques. This results in a significant cost reduction as compared to other manufacturing techniques. Also, it is not necessary that the CAM have a flat surface in a direction parallel to the rotation axis (i.e. the thin edge of the CAM). That is, the surface can be slightly rounded (along the spin axis) to simplify the machining process. This eliminates one axis in a multi-axis diamond turning machine and the need to have a slope to the facet in injection molding applications.

Figure 12:
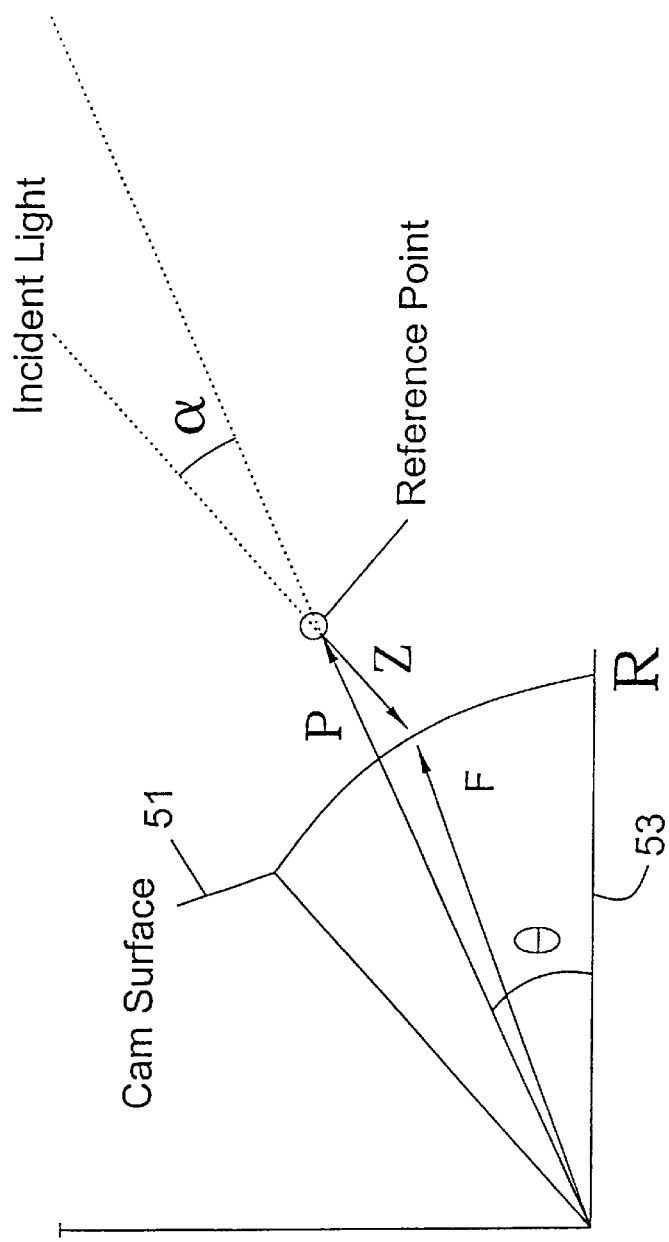
FIG. 12 shows an embodiment for one segment of the CAM surface, according to one embodiment of the invention.

FIG. 12 illustrates a preferred embodiment for one segment of the CAM surface 51. For simplicity, in this embodiment, we assume the use of a coordinate system in which the incident light moves, as opposed to moving the CAM.

Let P be a vector to a reference point through which the incident light traverses on its path to the CAM 50'. Let F be a vector that represents the point at which the incident light meets the CAM surface 51. Let Z be a vector that represents the longitudinal path-length increase as the CAM 50' is rotated by angle θ. Let α be the angle between the incident light and the x-axis when the rotation angle θ=0. For the CAM 50' to properly operate, the chief ray of the incident light must be retro-reflected off of the CAM surface 51 for any angle θ. Let R be the radius 53 of the CAM along the x-axis.

By inspection, $$P = R(\cos(\theta)X + \sin(\theta)Y) \quad \text{Equation 1}$$

$$F = P - Z \quad \text{Equation 2}$$

For a uniform velocity profile Z must be linearly increasing with θ by some constant k. Thus $$Z = -kR\theta[(\cos(\alpha+\theta))X + (\sin(\alpha+\theta))Y] \quad \text{Equation 3}$$

$$|Z| = kR\theta \quad \text{Equation 4}$$

Therefore $$F = R[\{\cos(\theta) - k\theta[\cos(\alpha+\theta)]\}X + \{\sin(\theta) - k\theta[\sin(\alpha+\theta)]\}Y] \quad \text{Equation 5}$$

$$|F| = R\text{sqrt}(1 - 2k\cos(\alpha)\theta + (k\theta)^2) \quad \text{Equation 6}$$

Let T be a vector that is tangent to the CAM surface of F. Then, $$T = dF/d\theta \quad \text{Equation 7}$$

To ensure that the light 195 intersecting the CAM surface 51 is retro-reflected back into the reference arm, the surface tangent T must be orthogonal to the light path Z. Thus the vector dot product of T and R must be zero. Thus, $$T \cdot R = 0 \quad \text{Equation 8}$$

Solving for this equation, it can be shown that $$\sin(\alpha) = k \quad \text{Equation 9}$$

Thus, in summary, equations describing the path-length increase in θ, and the CAM surface contour F, the magnitude of F, and the relationship between α and k, are given by, $$\Delta L = |Z| = kR\theta \quad \text{Equation 10}$$

$$F(\theta, k, \alpha) = \quad \text{Equation 11}$$
$$R[\{\cos(\theta) - k\theta[\cos(\alpha+\theta)]\}X + \{\sin(\theta) - k\theta[\sin(\alpha+\theta)]\}Y]$$

$$|F(\theta, k, \alpha)| = R\text{sqrt}(1 - 2k\cos(\alpha)\theta + (k\theta)^2) \quad \text{Equation 12}$$

$$\sin(\alpha) = k \quad \text{Equation 13}$$

As an example of a CAM system of interest to OCT systems, the following system is described (this CAM system is also cited elsewhere throughout the document). Typical polygonal scanner motors can run at between 5000 and 45000 RPM. To achieve a longitudinal reference arm scan rate of 2 kHz using a motor speed of 15,000 RPM, the system requires 8 CAM segments: 8*15,000/60=2 kHz. These polygonal scanner systems can accommodate a CAM radius 53 of R=1.5"=38.1 mm. Typical OCT biomedical imaging systems require a scan length of about 4 mm (3 mm of data plus 1 mm of extra window). Thus, $$R = 1.5" = 38.1 \text{ mm}$$

$$k = (4 \text{ mm}/38.1 \text{ mm})/(2p45°/360°) \sim 0.133673443$$

$$\alpha = \sin^{-1}(k) \sim 7.68191853° = 0.134074771°$$

$$F(\theta, k, \alpha) = 1.5"[\{\cos(\theta) - k(p\theta/180)[\cos(\alpha+\theta)]\}X + \{\sin(\theta) - k(p\theta/180)[\sin(\alpha+\theta)]\}Y]$$

θ is in degrees and varies from 0° to 45°

In one embodiment, a CAM was designed with a 0.625" hole in the center and three 0.120" through holes for mounting to the motor shaft. A groove was cut at approximately a 1" radius from the center and used for injecting epoxy to mass balance the CAM. This is just one embodiment of a wide variety of CAM parameters than can be manufactured. In manufacturing the CAM, it is useful, but not necessary, that the following conditions be met:

1) The CAM has nearly identical segments.
2) In z-axis, the CAM must be smooth to optical precision (not necessarily flat and perpendicular to the z-axis).
3) The radius of curvature at the step transitions should be minimized.
4) The surface should be cut with sufficient resolution to follow the ideal CAM surface contour, F (θ, k, α), to optical precision (e.g. ~1-wavelength over arcs).
5) Reflectivity for a spot focused on the surface as the CAM rotates from 0° to 360° must be nearly constant except near transitions between segments.

It should be noted that a preferred embodiment of this invention relates to calibrating the effects of CAM system imperfections in real-time (or non real-time). Algorithms can also be used to correct for intensity fluctuations. For example, FIG. 3 shows that there are power fluctuations across each segment of the CAM as the CAM surface 51 goes in and out of focus. Longer focal lengths reduce this fluctuation by increasing sensitivity to alignment errors (e.g. tilt). Since these intensity fluctuations can easily be recorded (or mathematically derived), they can be calibrated out in a manner similar to the surface irregularities, and can be calibrated on a pixel-by-pixel basis. Thus, in a preferred embodiment, the scan correction block corrects for both surface irregularities that give rise to spatial resolution degradation, as well as intensity fluctuations that would give rise to amplitude resolution degradation.

Other Embodiments

We have previously discussed the operation of a multi-segment CAM surface 51 for use in OCT systems. Other embodiments of this invention, however, encompass much to broader elements than a rotating CAM surface. In general, one preferred embodiment of this invention is directed to translating rotational motion into optical path-length scanning for high-resolution high-speed OCT imaging. This section describes other embodiments of this invention.

Figure 13A:
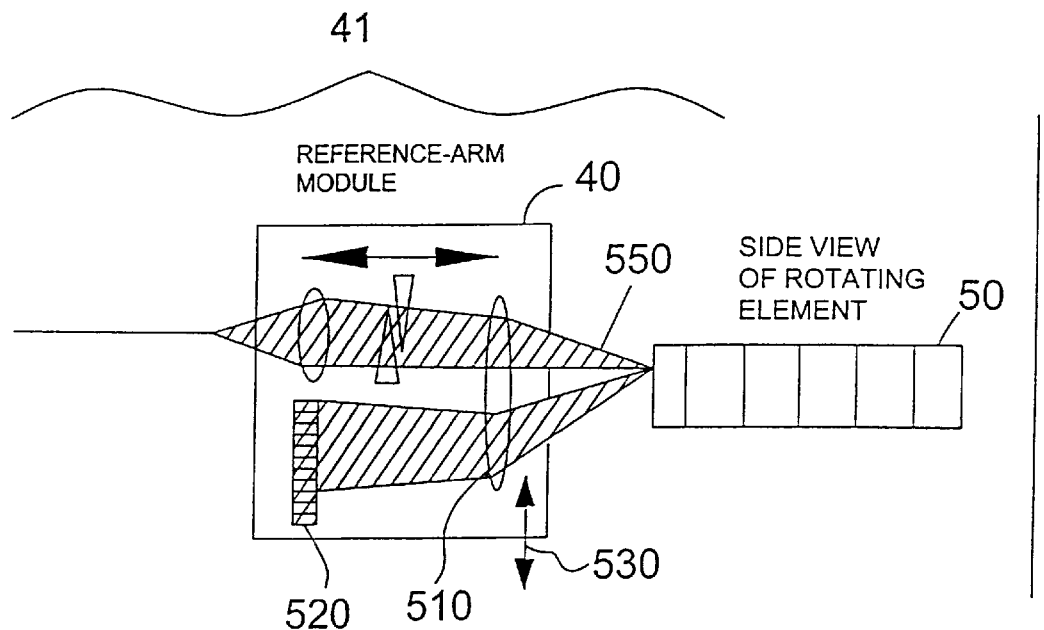
FIG. 13A is a drawing showing an embodiment of the use of the rotating element in a double-pass geometry to increase the depth of the scan.
Figure 13B:
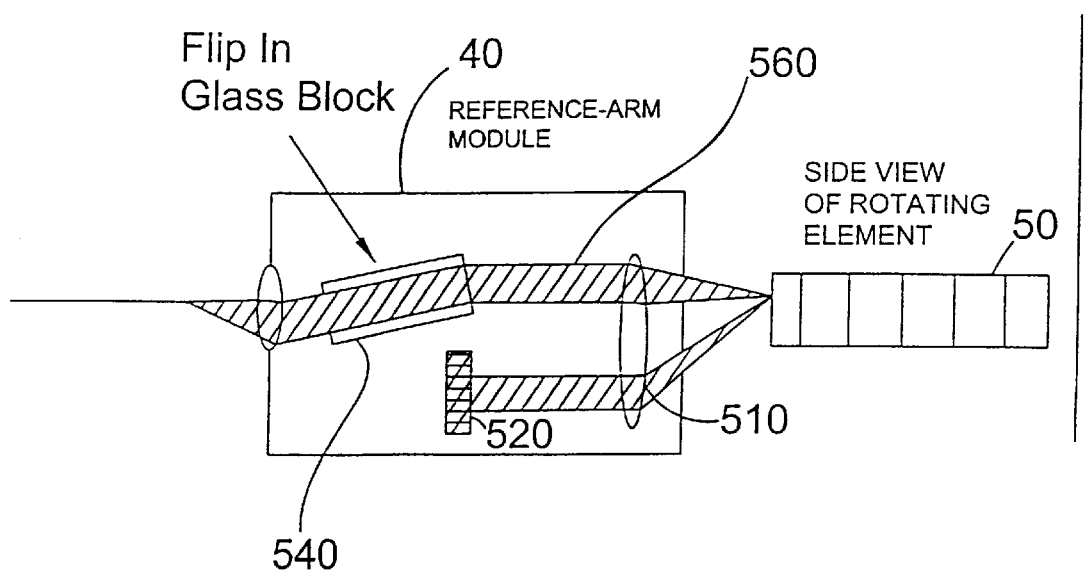
FIG. 13B is a drawing showing another embodiment of the use of the rotating element in a double-pass geometry to increase the depth of the scan.

FIGS. 13A and 13B are drawings which show an embodiment of the invention, with rotating element 50 arranged in double-pass geometry configuration. By using rotating element 50 in double-pass, twice the stroke can be achieved. Note that the Doppler shift will also be doubled, which must be accounted for in the signal processor. This effectively doubles the scan depth of the sample probe relative to single-pass geometry. The double-pass mechanism can either be put in reference module 40 or be separated from it as shown by the dashed lines in FIGS. 13A and 13B. Two embodiments of double-passing are shown here. In FIG. 13A, light 550 from the reference arm 41 is focused on rotating element 50 at a slight angle (exaggerated angle shown). The light 550 then reflects onto the lens 510 which collimates the light and sends it to a mirror 520, where it is retro-reflected and passes again across the rotating element surface back into the reference arm 41.

In this embodiment, it is desirable to use a longer confocal-parameter to minimize signal power loss. Note that by using a focusing lens with an increased depth-of-field, power fluctuations as the rotating element surface comes in and out of focus are minimized. In another embodiment of this invention, a mechanism exists to adjust the position of the lenses so that the light beam on rotating element 50 can, upon command, be automatically adjusted from single pass to double pass to allow the user more flexibility. This is indicated by the vertical arrow 530 on the focusing lens 510 of FIG. 13A.

Alternatively, as shown in FIG. 13B, another embodiment uses a block 540 which can be glass or another material, and which can be flipped into place using a mechanical pivot and a manual or automatic motor (solenoid) (not shown). The block 540 is arranged on an angle so that when the block 540 is in place, it raises the light 560 entering the focusing lens 510 for double pass operation. When the block 540 is out, the light 560 traverses the center of the lens 510 and operates in single pass mode. This embodiment has the attractive feature that, by choosing the angle and length of the block 540, the light can be precisely raised by moving the block 540 into place. Further, the light 560 is relatively insensitive to the precise positioning of the block 540. The adjustment of the glass block 540 can be made via a stepper motor, solenoid, electro-optic or other suitable means. Also, it is not necessary that only one lens be used for the double-pass geometry.

Figure 13C:
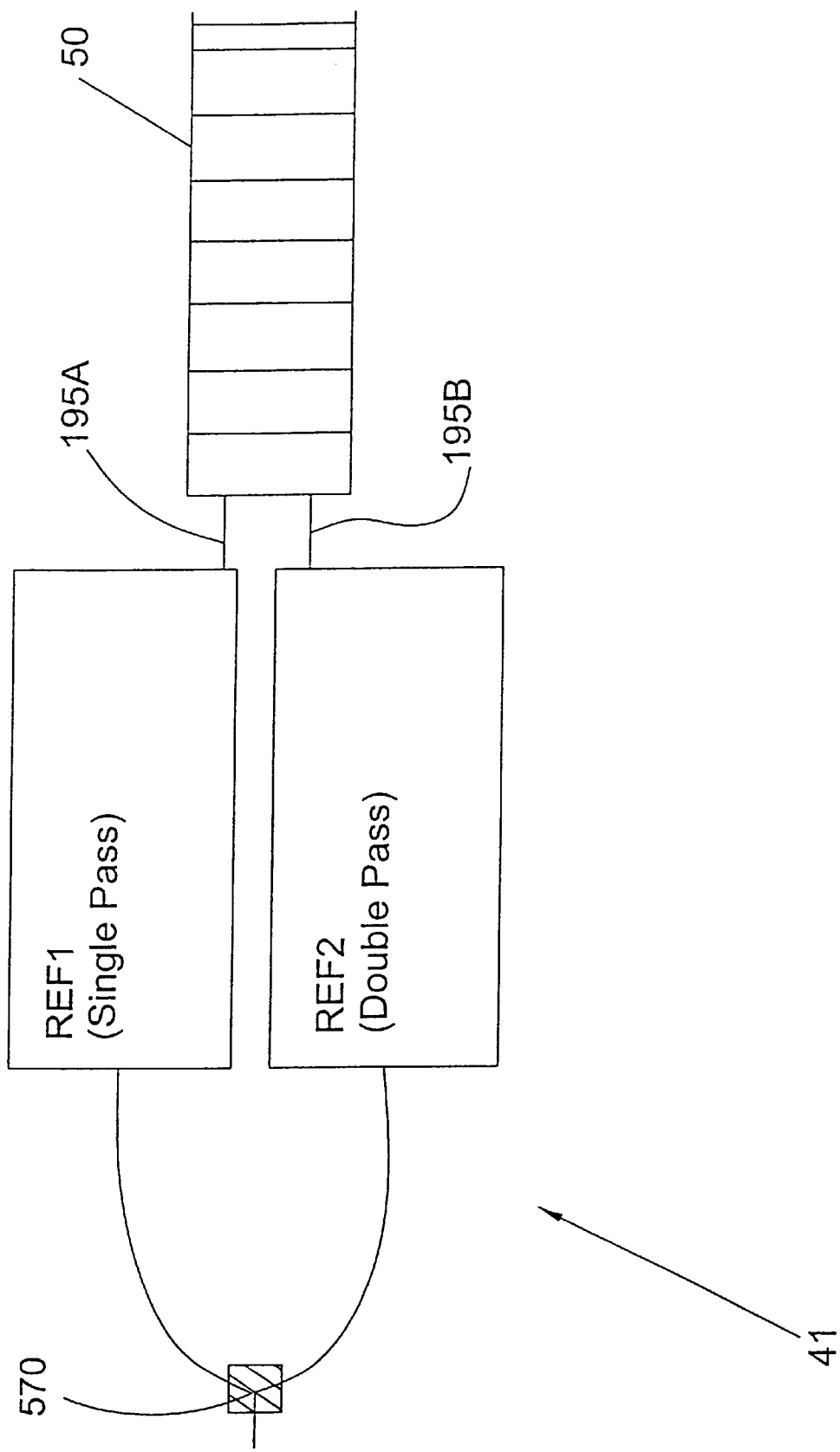
FIG. 13C is a drawing showing another embodiment of a double-pass configuration using two reference arms coupled with a fiber coupler.

FIG. 13C shows another embodiment for double-passing. In the previous embodiment, switching between single reflection and dual reflection operation involved motion of a lens. This requires the path-length adjustment mechanism to compensate for delay in the position of the reflection. Referring to FIG. 13C, another embodiment eliminates the delay by splitting the reference arm interferometer into two paths REF1 and REF2 using a fiber coupler 570, and aligning each fiber output 195A and 195B separately on rotating element 50. The first arm REF1 can be operated in single reflection mode, while the second arm REF2 can be aligned to a different section of the rotating element 50 and operated in double-pass reflection mode. The nominal delay in the single-pass arm and the double-pass are matched (in absolute delay at the center, or predetermined location, of the scan image and dispersion). The OCT instrument may switch between the two delays by using a mechanical shutter to block one or the other of the reference arms. Alternatively a 1:2 single-mode fiber optic switch can be used in place of the 50/50 fiber coupler 570. This latter approach eliminates the 6 dB loss in the reference arm reflected power. Since, however, there is typically excess reference arm power, performance will not be compromised.

Figure 13D:
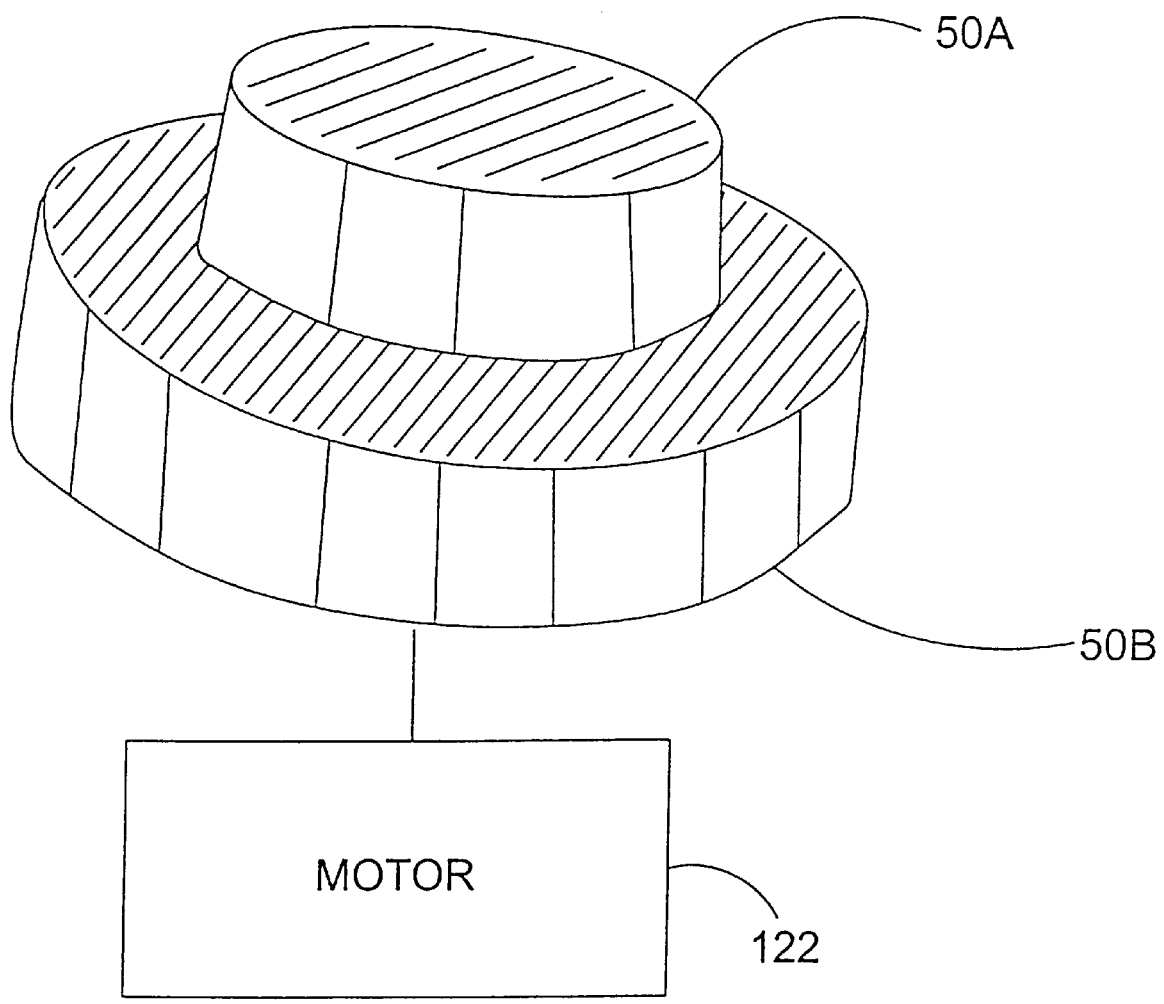
FIG. 13D shows an embodiment of this invention incorporating two or more CAMs with different scan depths, each mounted on top of the other.

Referring to FIG. 13D, another embodiment of this invention incorporates two or more rotating elements, for example CAMs 50A and 50B, with different scan depths, each mounted on top of the other and driven by the same motor 122. They need not, however, have different radii as shown. If the scan speed for the different CAMs is kept constant, the Doppler frequency can be left invariant, hence allowing for a simplified receiver design. This also has the advantage of leaving the aberration of the CAM surface constant. The table below shows examples. The product is a number proportional to the Doppler shift.

TABLE 1

|  | Number of facets | Delay per facet | Product |
| --- | --- | --- | --- |
| CAM 1 | 8 | 4 mm | 8 × 4 = 32 |
| CAM 2 | 4 | 8 mm | 4 × 8 = 32 |
| CAM 3 | 16 | 2 mm | 16 × 2 = 32 |

In this embodiment, CAMs 1 and 2 have commensurate synchronizations. That is, the position sensor of the 4 facet CAM can be read by dividing down the position sensor for the 8 facet CAM.

Alternatively, in another embodiment, the reference arm of the interferometer can be divided into two, as in the case described previously.

For simplicity, the previous discussion was directed primarily to the specific embodiment of a rotating element 50 as an OPS unit 175. It should be understood that the discussion applies to any of the specific OPS units discussed, or others known in the art.

Figure 14A:
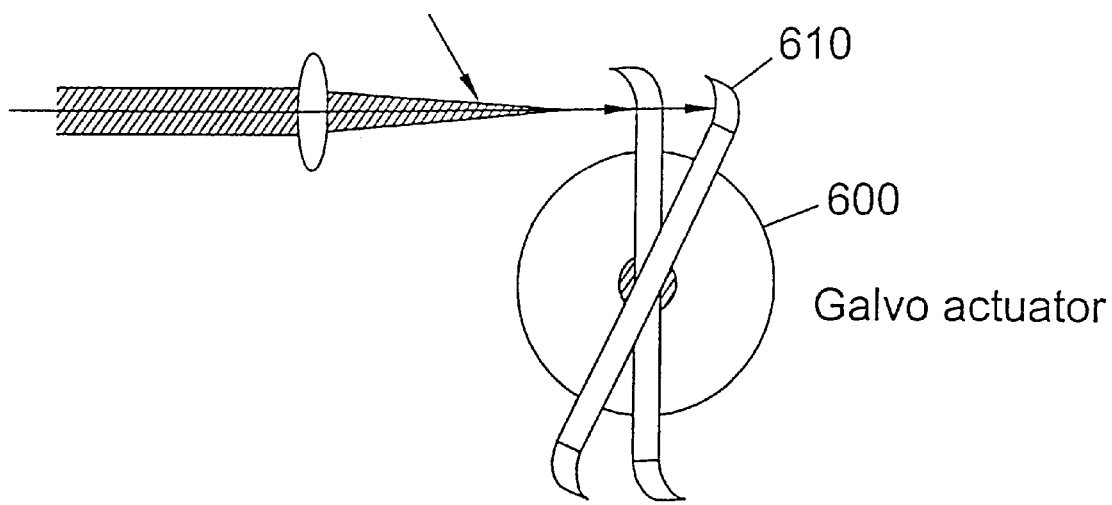
FIG. 14A is a drawing showing an embodiment including a Galvanometer and a custom mirror to perform linear translation.

FIG. 14A is a drawing showing another embodiment of the invention, using a Galvanometer 600 driven in linear translation stage, and using a custom mirror 610 to perform linear scanning. Most of today's commercial OCT methods use a small retro-reflector located on the end of a Galvanometer. This has two problems. First, the retro-reflector is massive and high speed can not be achieved. Second, the translation from angular motion of the Galvanometer shaft to displacement of the retro-reflector is not linear. By using nearly the same mathematical treatment described above for the CAM surface, a Galvanometer mirror surface can be derived to precisely translate shaft rotation to linear-mirror translation while maintaining the condition of retro-reflecting the light beam. This has the advantage over standard commercial techniques in that the mirror is lower in mass than a retro-reflector and can thus achieve higher speeds. Also, the translation from rotational motion to displacement of the focus can be made linear. In this example, the mirror 610 is rotated with a ramp or triangle waveform to achieve linear displacement in time.

Many of today's highest speed galvanometers are resonant galvanometers and can only be driven sinusoidally in time. These Galvanometers can be used if a Doppler tracking receiver is implemented in scan analyzer and correction unit 160. It is possible, however, to use a different mirror surface so as to produce a translation from sinusoidally angular rotation to linear displacement of the focus. That is, when the Galvanometer shaft is driven sinusoidally in time, a linear translation of the retro-reflected light beam is achieved. This produces a higher overall OCT system efficiency than can be achieved with a Doppler tracking receiver. Specifically, there is almost a six-times improvement in signal-to-noise ratio or image frame-rate for the same signal power. As a result, a high-speed low-cost reference arm translator for OCT systems can be achieved.

Figure 14B:
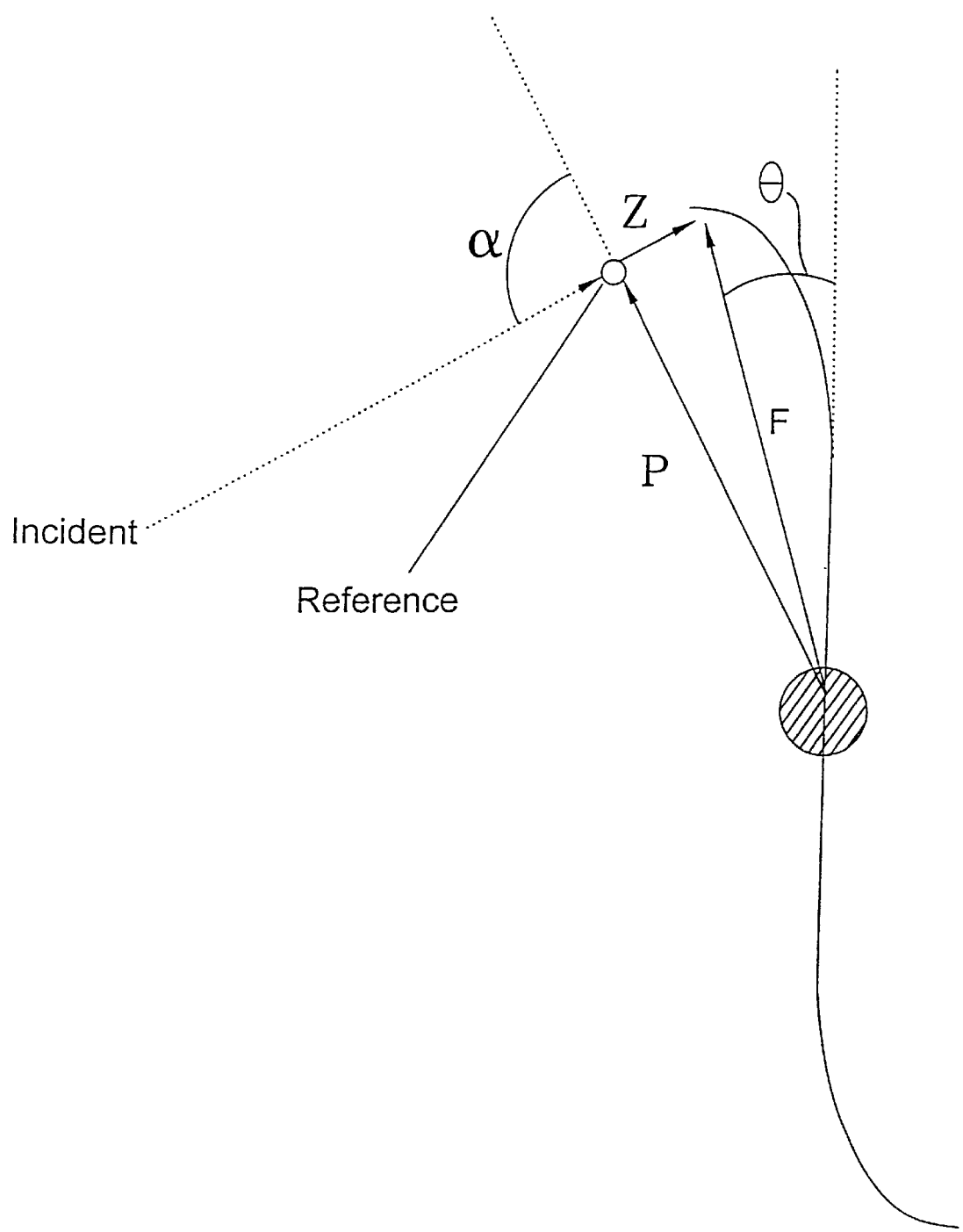
FIG. 14B is a drawing showing an embodiment including the mirror with the Galvanometer to perform linear translation.

In FIG. 14B, as the mirror is rotated, the path-length Z increases linearly in angle, and the chief ray is retro-reflected. The equations discussed above with respect to FIG. 12 can be used with the vectors as shown in FIG. 14B.

Figure 15:
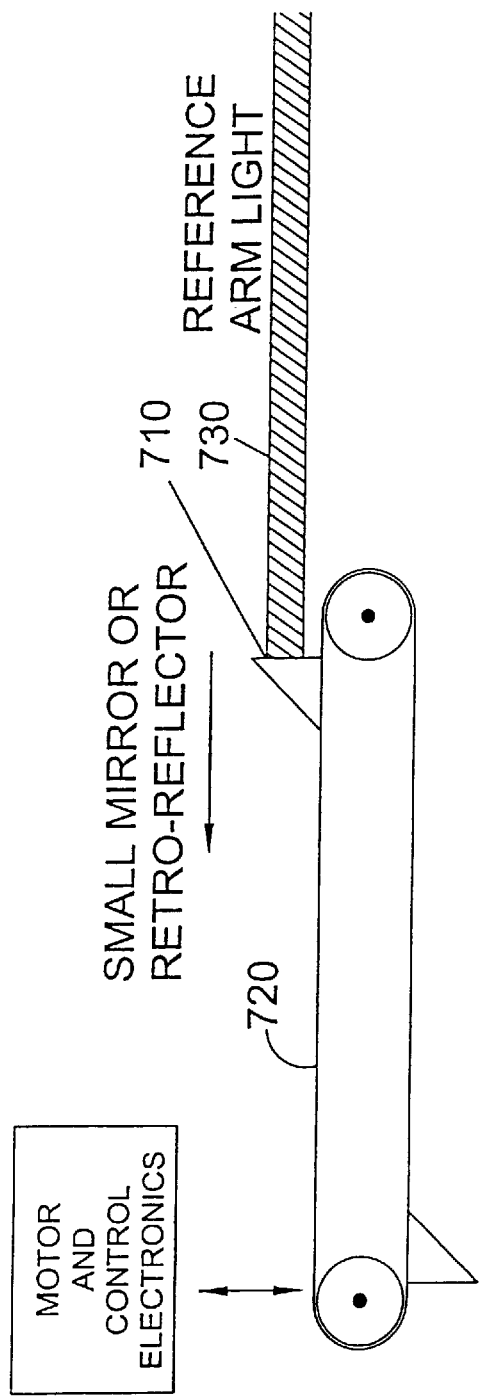
FIG. 15 is a drawing which shows an embodiment of the invention that uses small moving mirrors (or retro-reflectors) mounted on a rotating belt.

FIG. 15 is a drawing which shows another embodiment of the invention that uses small moving mirrors 710 or retro-reflectors mounted on a rotating belt 720. This embodiment, which is an example of another longitudinal scanning mechanism, has the potential for very-large strokes at high-speed. In this embodiment, the reference arm light beam 730 is directed onto a series of small moving mirrors 710 or retro-reflectors. As the surface is translated, the mirrors 710 are translated and the reference-arm path-length is translated. This device could be constructed on a small "conveyor belt like" device to allow a rotational motor to rapidly translate the mirrors. The spacing between mirrors can be adjusted to perform various duty cycle. Using this technique, large rapid displacements with minimal dead time can be achieved.

Figure 16:
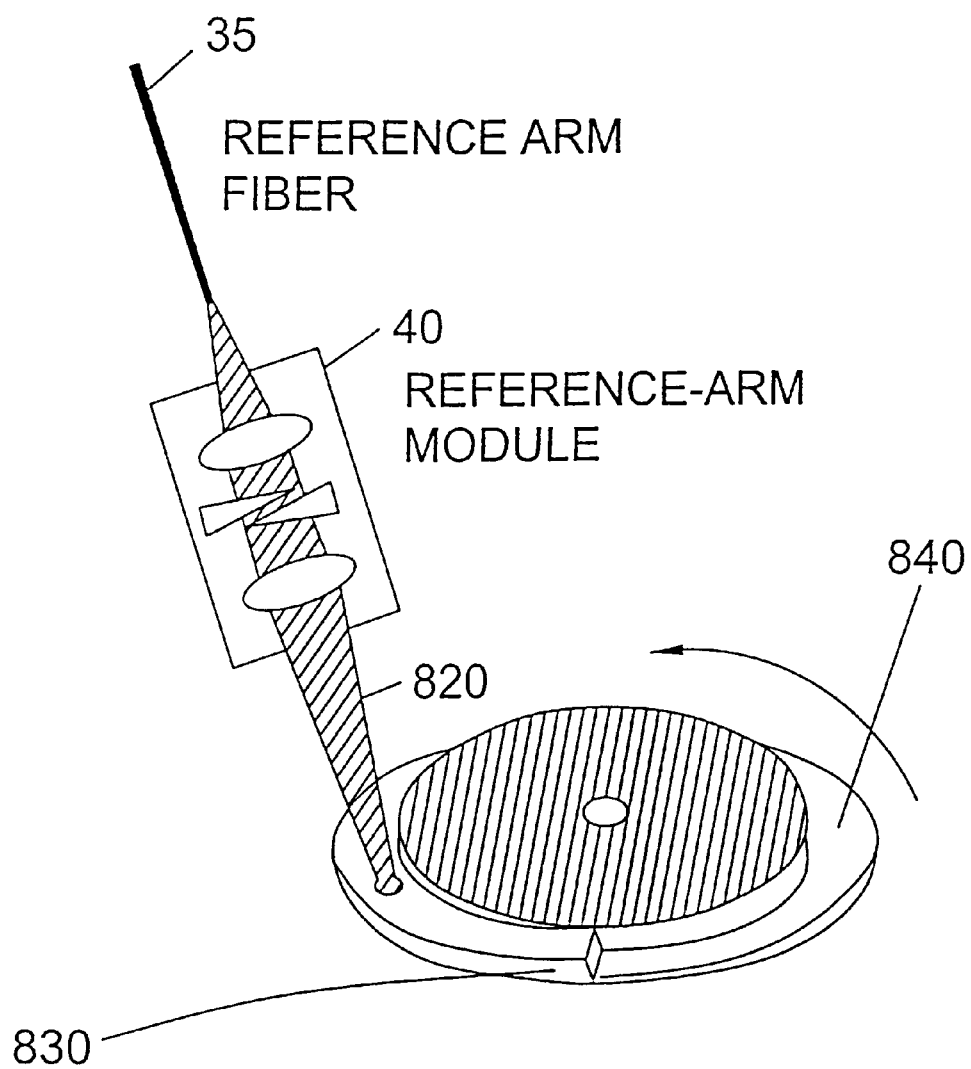
FIG. 16 is a drawing showing an embodiment of a rotation helical mirror.

FIG. 16 is shows another embodiment of this invention, using a rotational helical mirror. Here, the reference arm fiber 35 is connected to the reference-arm module 40 and the light 820 is focused on a rotating helical mirror 810. This device operates in a similar fashion as the CAM based designs, except the edge 830 of the spinning disc 810 is not used. Instead, the face 840 of the spinning disc 810 is used to vary the path-length of light. A set of mathematical expressions similar to those described above for the CAM can be derived to describe this embodiment. In one embodiment, the path-length increases linearly with rotation, and the chief (or central) ray of the focused light 820 is retro-reflected back into the reference arm fiber 35. In addition to the single segment mirror 810 shown, a multiple segment mirror can be used to achieve higher speeds. In most instances, due to manufacturing imperfections, a scan correction mechanism is needed to achieve high resolution. Thus, if the mirror has multiple segments, the machining imperfections in the surface can be calibrated and corrected in real-time (or non real-time) using an algorithm similar to those previously described.

Figure 17A:
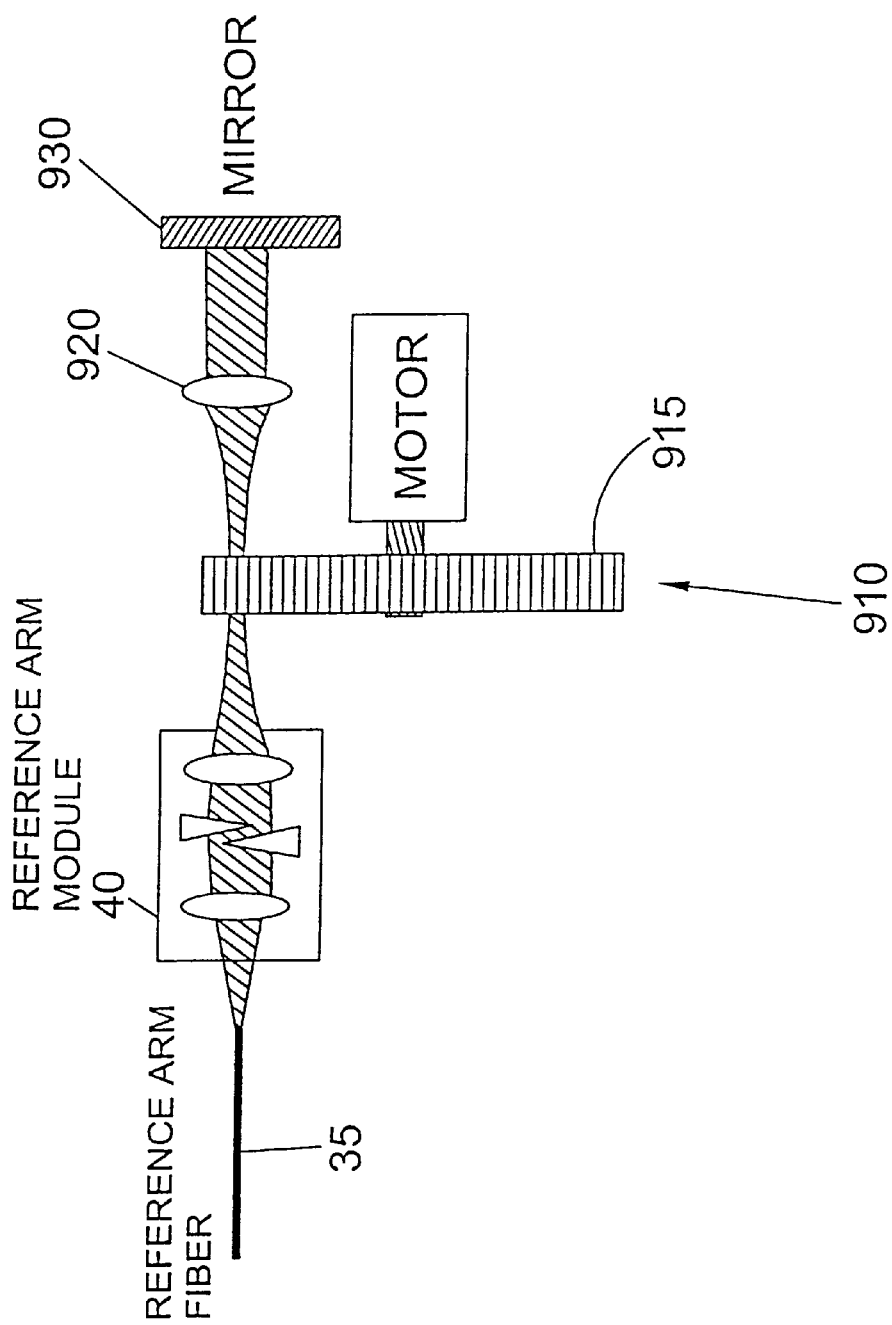
FIG. 17A is a drawing which shows an embodiment of the invention that uses a rotational Disc with varying index-of-refraction or thickness.
Figure 17B:
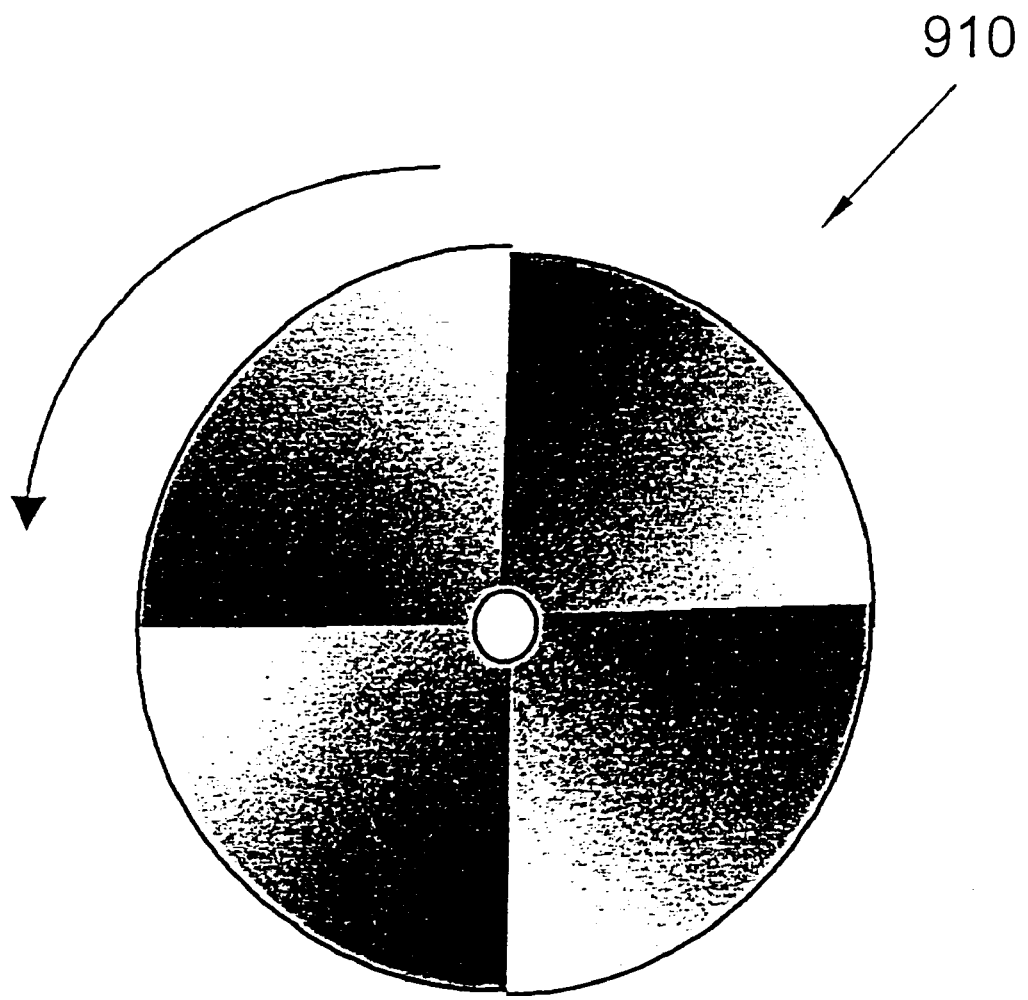
FIG. 17B is a drawing which shows an embodiment of the invention including a rotational disk with constant physical thickness and a radically varying index-of-refraction.

FIG. 17A shows another embodiment of this invention that uses a rotating disc 910 with either a varying index-of-refraction or a varying thickness to produce an OCT system with high-speed longitudinal scanning. In one embodiment, the rotating disc 910 can be transmissive. The light can be utilized after passing once through the disc 910, but preferably is reflected back through the disc 910 using lens 920 and mirror 930. Alternatively, the disc could have its second surface 915 mirrored so as to eliminate the need to the external lens 920 and mirror 930. Further, disc 910 can either have a physically varying thickness, or, as shown in FIG. 17B, a constant physical thickness and a angularly varying index-of-refraction. In another embodiment, the disc 910 could have both a physically varying thickness and a varying index-of-refraction. Thus, in any variation, as disc 910 is spun, the optical path-length varies. In one embodiment, as the disc is rotated with a uniform angular velocity, a nearly-uniform increase in optical path-length is achieved.

Such a design could also be used in an interferometric embodiment that is transmissive (e.g. Mach/Zehnder Interferometer) as opposed to a Michelson interferometer.

Other Applications

It should be noted that the various embodiments of this invention turn high-speed nearly-continuous rotational motion into precise nearly-linear longitudinal path-length motion.

The foregoing embodiments are merely exemplary and are not to be construed as limiting the present invention. The present teaching can be readily applied to other types of apparatuses. This invention has several other uses outside the field of OCT, including optical autocorrelators for femp-tosecond optics, high-speed wave meters, laser-radar, and others. This device can also be used within a laser cavity (such as a Fabry-Perot Laser) to rapidly and smoothly tune the laser output frequency. The description of the present invention is intended to be illustrative, and not to limit the scope of the claims. Many alternatives, modifications, and variations will be apparent to those skilled in the art.

What is claimed is:

1. An apparatus, comprising:
   an interferometer which receives broadband light and outputs a reference output signal and a probe signal directed to a sample which produces a sample return signal;
   an optical path-length scanning unit which receives the reference output signal from the interferometer and outputs a reference return signal to said interferometer, said interferometer combining the reference return signal and the sample return signal and outputting an interferometer output signal;
   a detector unit which receives the interferometer output signal and outputs a detector output signal;
   a scan analyzer and correction unit coupled to said detector unit that receives the detector output signal; and
   a scanning unit controller coupled to an optical path-length scanning unit, said scanning unit controller controls said optical path-length scanning unit and outputs a controller signal to said scan analyzer and correction unit, wherein said scan analyzer and correction unit analyzes the controller signal and the detector output signal and determines scan correction information.

2. The apparatus of claim 1, wherein said scan analyzer and correction unit comprises an optical path-length position unit which receives the controller signal and detector output signal and generates scan correcting data.

3. The apparatus of claim 2, wherein said optical path-length position unit comprises a scan correction unit and a marker detector, wherein said marker detector receives said controller signal and outputs marker information to said scan correction unit which analyzes said detector output signal and said marker information and outputs said scan correction data.

4. The apparatus of claim 3, wherein said scan analyzer and correction unit further comprises a signal correction processor which receives said scan correction data and modifies said detector output signal using said scan correction data and outputs scan corrected sample data.

5. The apparatus of claim 1, wherein the optical path-length scanning unit comprises a rotating element.

6. The apparatus of claim 5, wherein said rotating element comprises a CAM.

7. The apparatus of claim 1, wherein said optical path-length scanning unit comprises a reflecting surface and said scanning unit controller includes a galvanometric motor.

8. The apparatus of claim 1, wherein said interferometer comprises a double-pass unit.

9. The apparatus of claim 1, wherein said optical path-length scanning unit comprises a rotating helical mirror.

10. The apparatus of claim 9, wherein said rotating helical mirror has a depth which varies approximately linearly in time when driven at an approximate constant rotational speed.

11. The apparatus of claim 1, wherein said optical path-length scanning unit comprises a rotating disc.

12. The apparatus of claim 11, wherein said rotating disc is transmissive.

13. The apparatus of claim 11, wherein said rotating disc is reflective.

14. The apparatus of claim 11, wherein said rotating disc has an index-of-refraction that varies with angle of rotation.

15. The apparatus of claim 1, wherein the said optical path-length scanning unit comprises a translational element.

16. The apparatus of claim 1, wherein the said optical path-length scanning unit comprises a rotating element and a translational element.

17. The apparatus of claim 1, wherein said optical path-length scanning unit comprises a reflective surface mechanically coupled to a rotating belt.

18. The apparatus of claim 1, further comprising a coarse path-length adjustment mechanism.

19. An apparatus, comprising:
an interferometer which receives broadband light and outputs a reference output signal and a probe signal directed to a sample which produces a sample return signal;
a rotating optical path-length scanning unit which receives the reference output signal and outputs a reference return signal to said interferometer, said interferometer combining the reference return signal and the sample return signal and outputting an interferometer output signal;
a detector unit for receiving the interferometer output signal and outputting a detector output signal;
scan analyzer and correction unit coupled to said detector unit including an optical path-length position unit for receiving the detector output signal; and
scanning unit controller coupled to said rotating optical path-length scanning unit, for controlling said rotating optical path-length scanning unit and for outputting a controller signal to said scan analyzer and correction unit, wherein said scan analyzer and correction unit analyzes the controller signal and the detector output signal and determines scan correction information.

20. The apparatus according to claim 1, wherein the optical path length scanning unit substantially retro-reflects the reference output signal received from the interferometer to output a reference return signal to said interferometer.

21. The apparatus according to claim 19, wherein the rotating optical path length scanning unit substantially retro-reflects the reference output signal received from the interferometer to output a reference return signal to said interferometer.

22. The apparatus according to claim 5, wherein the rotating element comprises micro retro-reflectors.

23. The apparatus according to claim 19, wherein the rotating optical path-length scanning unit comprises a rotating element having micro retro-reflectors.

* * * * *